United States Patent [19]

Hester, Jr.

[11] 4,081,452
[45] Mar. 28, 1978

[54] NOVEL DERIVATIVES OF 4H-S-TRIAZOLO[4,3-α][1,4]BENZODIAZEPINES

[75] Inventor: Jackson B. Hester, Jr., Galesburg, Mich.

[73] Assignee: The Upjohn Company, Kalamazoo, Mich.

[21] Appl. No.: 713,925

[22] Filed: Aug. 12, 1976

Related U.S. Application Data

[62] Division of Ser. No. 666,902, Mar. 15, 1976, Pat. No. 4,009,175.

[51] Int. Cl.$^2$ ............................................. C07D 487/04
[52] U.S. Cl. ................................. 260/296 T; 424/263;
424/269; 260/294.8 B; 260/294.8 C; 260/294.8 R; 260/308 R
[58] Field of Search ........... 260/308 R, 240 G, 296 B, 260/296 T

[56] References Cited
U.S. PATENT DOCUMENTS

| | | | |
|---|---|---|---|
| 3,681,343 | 8/1972 | Hester | 260/239.3 T |
| 3,842,090 | 10/1974 | Gall | 260/247.1 |
| 3,912,753 | 10/1975 | Hester | 260/308 R |
| 3,966,943 | 6/1976 | Hester | 424/263 |
| 4,009,175 | 2/1977 | Hester | 260/296 T |

OTHER PUBLICATIONS

Smith, The Chemistry of Open-Chain Organic Nitrogen Compounds, vol. II, frontispage and pages 29 to 30, W. A. Benjamin, Inc. (NY) 1966.

*Primary Examiner*—John D. Randolph
*Attorney, Agent, or Firm*—Hans L. Berneis

[57] ABSTRACT

Compounds of the formula:

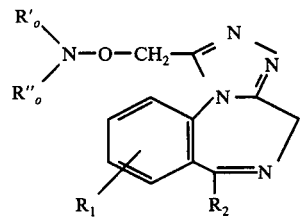

wherein $R'_o$ and $R''_o$ are hydrogen or alkyl of 1 to 3 carbon atoms, inclusive; $R_1$ is hydrogen, fluoro, chloro, bromo, nitro, trifluoromethyl, or alkylthio in which the alkyl moiety is of 1 to 3 carbon atoms, inclusive; $R_2$ is phenyl, o-chlorophenyl, o-fluorophenyl, 2,6-difluorophenyl and 2-pyridyl are prepared by multistep reactions from compounds of formula I:

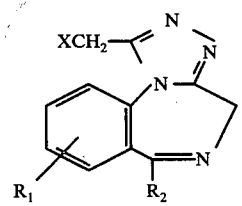

wherein $R_1$ and $R_2$ are defined as above and X is chlorine or bromine.

Compounds of formula III, intermediates in the preparation thereof, Schiff's bases of compounds IIIA (III in which $R'_o$ and $R''_o$ are hydrogen), and the pharmacologically acceptable acid addition salts are useful in birds and mammals, including man, as sedatives, antianxiety, antidepressant, anticonvulsive, and muscular relaxing agents.

8 Claims, No Drawings

NOVEL DERIVATIVES OF 4H-S-TRIAZOLO[4,3-a][1,4]BENZODIAZEPINES

This is a division of application Ser. No. 666,902, filed Mar. 15, 1976, now U.S. Pat. No. 4,009,175, granted Feb. 22, 1977.

BACKGROUND OF THE INVENTION

1. Field of the Invention

This invention is directed to new 1-[(aminooxy)methyl]-6-substituted-4-H-s-triazolo[4,3-a][1,4]benzodiazepines, intermediates, and the processes of production thereof.

The novel compounds and the processes of the production therefor can be illustratively represented as follows:

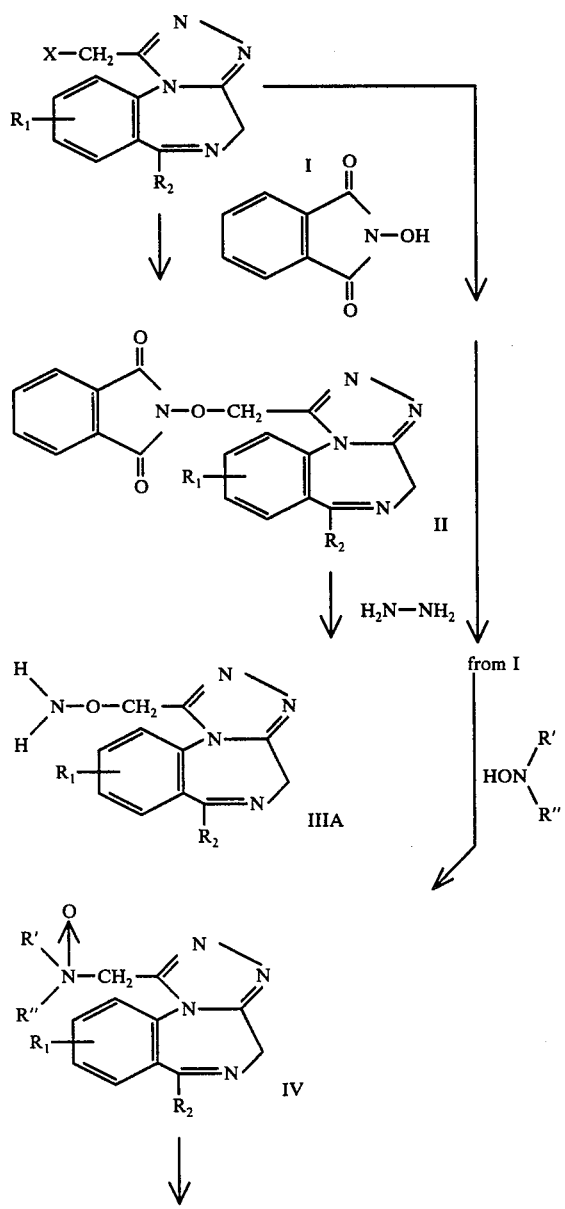

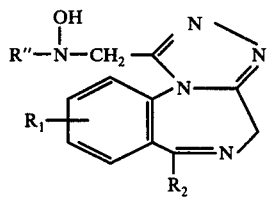

and if R' and/or R" is of 2 or 3 carbon atoms, inclusive,

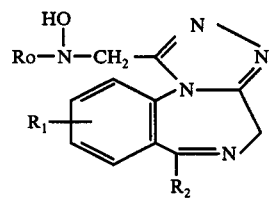

wherein R' and R" are alkyl of 1 to 3 carbon atoms, inclusive; wherein R'" corresponds to R' or R" with the proviso that R" or R' has 2 or 3 carbon atoms, inclusive; wherein $R_1$ is hydrogen, fluoro, chloro, bromo, nitro, trifluoromethyl or alkylthio in which the alkyl moiety is of 1 to 3 carbon atoms, inclusive; and wherein $R_2$ is phenyl, o-chlorophenyl, o-fluorophenyl, 2,6-difluorophenyl, or 2-pyridyl.

Compound IIIB is produced from IV if R' and R" are methyl, if R' and/or R" are alkyl of 2 to 3 carbon atoms, then simultaneously with IIIB compound V is obtained. Compounds of formula VA:

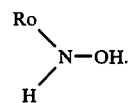

wherein $R_1$ and $R_2$ are defined as herein above and wherein $R_0$ is hydrogen or alkyl of 1 to 3 carbon atoms, inclusive; can also be prepared by reacting compound I with a hydroxyamine of the formula:

$$\begin{array}{c} Ro \\ \diagdown \\ N-OH. \\ \diagup \\ H \end{array}$$

The invention also embraces the pharmacologically acceptable addition salts of the compounds IIIA and IIIB as well as those of compounds IV, V and VA and the Schiff's bases derived from compound IIIA having the formula VI:

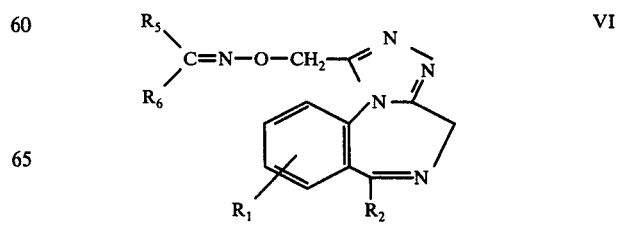

wherein $R_1$ and $R_2$ are defined as above and $R_5$ and $R_6$ are hydrogen or alkyl as defined above.

Thus the invention comprises compounds of formula III (composite formula of IIIA and IIIB):

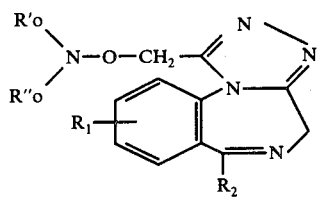

wherein $R'_0$ and $R''_0$ are hydrogen or alkyl of 1 to 3 carbon atoms, inclusive; $R_1$ is hydrogen, fluoro, chloro, bromo, nitro, trifluoromethyl, or alkylthio in which the alkyl moiety is of 1–3 carbon atoms, inclusive; $R_2$ is phenyl, o-chlorophenyl, o-fluorophenyl, 2,6-difluorophenyl or 2-pyridyl, and the pharmacologically acceptable acid addition salts thereof.

The invention further comprises the Schiff's bases of formula VI, the hydroxyamines of formulae V and VA and the intermediates of formula IV as well as the pharmacologically acceptable acid addition salts of compounds of formulae IV, V, VA, and VI.

The invention also comprises the processes of production for compounds III, IV, V, VA, and VI.

The process to produce the compounds of formula IIIA (i.e. compounds of formula III, wherein $R'_0$ and $R''_0$ are both hydrogen) comprises: treating a compound of formula I with N-hydroxyphthalimide in the presence of a tertiary amine base at 0° to 100° C. to obtain compound II; and treating compound II with hydrazine or its hydrate between 25°–100° C. to obtain compound IIIA.

The process to produce the compounds of formula IIIB (i.e. compounds of formula III, wherein $R'_0$ and $R''_0$ are alkyl of 1 to 3 carbon atoms, inclusive) comprises: treating compound I with a N,N-dialkylhydroxyamine and an acid neutralizing agent at 25° to 100° C. to obtain compound IV; heating compound IV between 140° to 200° C. to obtain compound IIIB, and if $R'$ and/or $R''$ is ethyl, propyl, or isopropyl, compound V.

Compounds of formula VA (compounds of formula V in which $R''$ is also hydrogen) are perpared by condensing a compound of formula I with an unsubstituted or N-monoalkylhydroxyamine.

The process to produce the compounds of formula VI comprises: condensing a compound of formula IIIA with an aldehyde or keto compound at temperatures of 0° to 100° C.

DESCRIPTION OF THE PREFERRED EMBODIMENT

Alkyl groups of 1 to 3 carbon atoms, inclusive, means methyl, ethyl, propyl, or isopropyl.

The more preferred compounds of formula III have the specific structure IIIC:

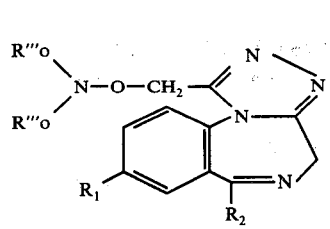

wherein $R''_0$ is hydrogen, methyl, or ethyl; wherein $R_1$ is hydrogen, fluoro, chloro, bromo, nitro, trifluoromethyl, or alkylthio in which the alkyl moiety is of 1 to 3 carbon atoms inclusive; and wherein $R_2$ is phenyl, o-chlorophenyl, o-fluorophenyl, 2,6-difluorophenyl or 2-pyridyl; and the pharmaceutically acceptable acid addition salts thereof.

Similarly more preferred are the species in the series of compounds IV, V and VA which have the formulae IVA and VB:

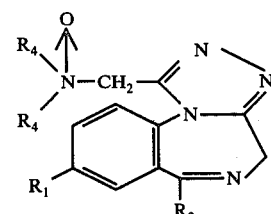

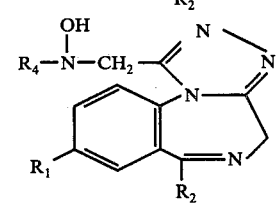

wherein $R_1$ is hydrogen, fluoro, chloro, bromo, nitro, trifluoromethyl, or alkylthio in which the alkyl moiety is of 1 to 3 carbon atoms, inclusive; wherein $R_2$ is phenyl, o-chlorophenyl, o-fluorophenyl, 2,6-difluorophenyl, or 2-pyridyl; and wherein $R_4$ is methyl or ethyl, and the pharmaceutically acceptable acid addition salts thereof.

The most preferred compounds of formula III have the specific structure IIID:

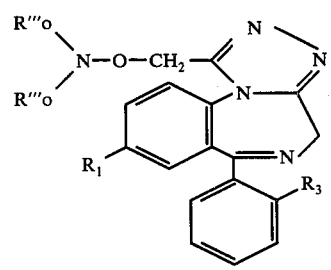

wherein $R_1$ is hydrogen, fluoro, chloro, or trifluoromethyl; wherein $R''_0$ is hydrogen, methyl, or ethyl; and wherein $R_3$ is hydrogen, chloro, or fluoro; and the pharmaceutically acceptable acid addition salts thereof.

Similarly most preferred are the species in the series of compounds IV, V and VA which have the formulae IVB and VC:

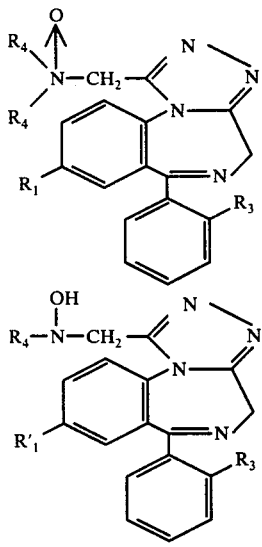

wherein R'₁ is hydrogen, chloro, or trifluoromethyl; wherein R₃ is hydrogen, chloro, or fluoro; and wherein R₄ is methyl or ethyl, and the pharmaceutically acceptable acid addition salts thereof.

The compounds of formula III (inclusive IIIA, B, C, and D), IV (inclusive of IVA and B), V (inclusive of VA, VB, and VC) and VI and the pharmacologically acceptable acid addition salts thereof, are useful sedative tranquilization and anti-anxiety agents for mammals, including man and birds. They also have antidepressant activity and can be thus used in man for the treatment of anxieties and endogenous and exogenous depressions.

The pharmacologically acceptable acid addition salts of the compounds III, IV, V, and VI including the preferred subclasses, include the hydrochlorides, hydrobromides, hydriodides, sulfates, phosphates, acetates, propionates, lactates, maleates, malates, succinates, tartrates, and the like.

The tranquilization and sedative activity of the new compounds of formulae III, IV, V, and VI (including the preferred subclasses) and their pharmacologically acceptable acid addition salts are tested in mice as follows:

Chimney test: [Med. Exp. 4, 145 (1961)]: The test determines the ability of mice to back up and out of a vertical glass cylinder within 30 seconds. At the effective dosage, 50% of the mice failed doing it.

Dish test: Mice in Petri dishes (10 cm. diameter, and 5 cm. high), partially embedded in wood shavings, climb out in a very short time, when not treated. Mice remaining in the dish for more than 3 minutes indicates tranquilization. ED₅₀ equals the dose of test compound at which 50% of the mice remain in the dish.

Pedestal test: The untreated mouse leaves the pedestal in less than a minute to climb back to the floor of the standard mouse box. Tranquilized mice will stay on the pedestal for more than one minute.

Nicotine antagonism test: Mice in a group of 6 are injected with the test compound. Thirty minutes later the mice including control (untreated) mice are injected with nicotine salicylate (2 mg./kg.). The control mice show overstimulation, i.e. (1) running convulsions, followed by (2) tonic extensor fits; followed by (3) dealth. Pretreatment with an active sedative or tranquilizing compound protects mice against (2) and (3).

TESTING FOR ANXIETY

Prolongation of Hypoxic survival

Pretreatment of mice exposed to the stress of progressive hypoxia and hypercapnia with anxiolytics results in a prolongation of survival.

Male CF-1 derived mice are used in these studies. Thirty minutes after intraperitoneal pretreatment (test agent suspended in 0.25% methylcellulose or vehicle alone, 1 cc/100 gm. body weight) the mice are placed singly in 125 ml. Erlenmeyer flasks. The receptacles were tightly stoppered and the survival time (time from stoppering to the last respiratory effort) of each animal noted. Each compound is tested at three or more doses spaced at 0.3 log intervals. Six mice are used per dose with six vehicle injected controls run simultaneously. The mean (15–18 minutes) and standard deviation (1–2 minutes) of the survival time for the vehicle treated mice are used to convert the data to a quantal form in the following manner. All survival times that differed from the mean of the controls by more than 2 standard deviations are scored as a drug effect. $ED_{50}$s are calculated by the method of Spearman and Karber (Finney, D. J., Statistical Method in Biological Assay, Hafner Publ., Co., N.Y., 1952).

The novel compounds of formula III (including compounds IIIA, IIIB, IIIC, IIID), IV (including IVA, IVB), V (including VA, VB, VC), and VI and pharmacologically acceptable acid addition salts thereof also have anti-depressant activity.

The main function of an anti-depressant is to return the depressed individual to normal function. This should be carefully differentiated from psychic stimulants such as the amphetamines which produce overstimulation in the normal individual.

Many different methods have been and are used to evaluate anti-depressant activity. In general these methods involve antagonism to a depressant such as reserpine or tetrabenazine or a synergistic increase of the toxicity of certain compounds (i.e., yohimbine or 3,4-dihydroxyphenylalanine) and comparison of the drug action of the new compound with other known anti-depressants. No single test alone can determine whether or not a new compound is an antidepressant or not, but the profile evidenced by various tests will establish that anti-depressant action is present. A number of such tests are described below.

Hypothermic tests with oxotremorine [1-[4-(pyrrolidinyl)-2-butynyl]-2-pyrrolidinone].

Oxotremorine (as well as apomorphine and tetrabenazine) produces hypothermic responses in mice. This response is blocked by anticholinergics and anti-depressants such as atropine and imipramine.

Oxotremorine produced a very pronounced hypothermia which reaches a peak 60 minutes after administration. When administered at 0.6 mg./kg. the body temperature of a mouse is decreased about 13° F. (when the mouse is kept at room temperature). This temperature decrease is antagonized by anti-depressants, e.g., desipramine, imipramine, and amitriptyline.

The present compounds are tested as follows. Groups of four male mice weighing 18–22 g. (Strain CF1, Carworth Farms) are injected intraperitoneally with the test compound prepared in 0.25% methylcellulose and placed in plastic cages. Thirty minutes later 1 mg./kg.

oxotremorine hydrochloride is injected subcutaneously. The mice are placed in a refrigerator maintained at 19° C. Thirty minutes later the intraperitoneal temperature is measured using a thermistor probe. An increase of 4° F. in the body temperature of the treated mouse (oxotremorine and test compound) over the control mouse (oxotremorine treated only) is indicative of antidepressive activity.

The same compounds were also tested for potentiation of yohimbine aggregation toxicity. The $LD_{50}$ of yohimbine hydrochloride in mice is 45 mg./kg. i.p. Administration of 20 mg./kg. of yohimbine hydrochloride is non-lethal. If an antidepressant is administered prior to the yohimbine hydrochloride (20 mg./kg.) the lethality of the yohimbine hydrochloride is increased.

Eight male CF1 mice, 18-22 g., are injected with yohimbine hydrochloride in saline solution. After four hours the $LD_{50}$s are determined. Groups of eight mice are injected with the antidepressant 30 minutes before the administration of yohimbine hydrochloride [YCl;] (20 mg./kg.). No mice or only one mouse is killed from 20 mg./kg. of [YCl]. If [YCl] is administered in the presence of an anti-depressant an increase in the toxicity of [YCl] is found. The $ED_{50}$ is the dosage of test compound which causes 50% of the mice to die.

Also the compounds are tested for the potentiation of apomorphine gnawing. A group of 4 mice (male, CF1, 18-22 g.) are administered the test compound intraperitoneally 1 hour prior to the subcutaneous injection of apomorphine hydrochloride 10 mg./kg. The mice are then placed in a plastic box (6 × 11 × 5 inches) lined at the bottom with a cellophane-backed, absorbent paper. The degree of damage to the paper at the end of 30 minutes is scored from zero to 4. The scores 2 to 4 indicate that the compound is a potentiator of apomorphine in this test.

Results in the above tests show that the compounds of formulae III to VI and the pharmacologically acceptable acid addition salts thereof can be used as antidepressants, sedatives, and anti-anxiety drugs in mammals to achieve normalcy in the depressed or anxious individual.

The pharmaceutical forms of compounds of formulae III to VI and salts thereof contemplated by this invention include pharmaceutical compositions suited for oral, parenteral, and rectal use, e.g., tablets, powder packets, cachets, dragees, capsules, solutions, suspensions, sterile injectable forms, suppositories, bougies, and the like. Suitable diluents or carriers such as carbohydrates, lactose, proteins, lipids, calcium phosphate, cornstarch, stearic acid, methylcellulose and the like may be used as carriers or for coating purposes. Water or oils such as coconut oil, sesame oil, safflower oil, cottonseed oil, and peanut oil, may be used for preparing solutions or suspensions of the active drug. Sweetening, coloring and flavoring agents may be added.

For mammals, food premixes with starch, oatmeal, dried fishmeat, fishmeal, flour, and the like can be prepared.

As antidepressants, sedatives, and antianxiety agents the compounds of formulae III through VI and their pharmacologically acceptable acid addition salts can be used in dosages of 0.02-1 mg./kg. and preferably 0.02-0.5 mg./kg. in oral or injectable preparations, as described above, to alleviate depression and anxieties occurring in stressful situations. Such situations are those for example, when animals are in travel or changing ownerships or are temporarily put into kennels, while their owners are absent from home. The larger mammals (10 kg. or more) respond best to the low dosages of the above dosage ranges.

The starting materials of formula I of this invention are 1-haloalkyl-6-phenyl or 6-(2-pyridyl)-4H-s-triazolo[4,3-a][1,4]benzodiazepines, which are described in British Specification No. 1,331,917 or are synthesized as shown in the Preparations.

In carrying out the process of this invention to synthesize compounds of the structure IIIA, a selected starting compound I is reacted with N-hydroxyphthalimide in the presence of a tertiary amine base, e.g. triethylamine, tripropylamine, diethylpropylamine, pyridine, N-methylpiperidine or the like, with triethylamine preferred. The reaction can be carried out between 0° to 100° C. during a period of 1 to 24 hours. Preferably room temperature, 18°-30° C. is used whereby the reaction is completed in 2 to 10 hours. Also preferred is an inert organic solvent such as dimethylformamide, diethylformamide, dimethylacetamide, dimethyl sulfoxide or hexamethyl phosphoric acid triamide. The product II is isolated and purified by conventional means, such as evaporating the solvent, or extracting product II, washing it, crystallizing or chromatographing it, and the like.

Compound II is then treated with hydrazine, hydrazine hydrate, or a primary alkyl amine, e.g. methyl, ethyl, or propyl amine or the like in a lower alkanol of 1 to 3 carbon atoms at 25°-100° C. Methanol, ethanol, or propanol are the preferred solvents, but tetrahydrofuran, dioxane, diethylether and the like can also be used. After the reaction is completed (1 to 10 hours), the product IIIA is obtained by conventional procedures, e.g. extraction, chromatography, crystallization and the like.

To obtain the products IV, a starting compound of formula I is treated with a N,N-dialkylhydroxyamine in which the alkyl groups are of 1 to 3 carbon atoms, inclusive. In the preferred embodiment of this invention an inert organic solvent is used e.g. dimethylformamide, dimethylacetamide, tetrahydrofuran, dioxane, dimethylsulfoxide, hexamethyl phosphoric acid triamide, methanol, ethanol, propanol, or the like at a temperature of 25° to 100° C for 1 to 24 hours. Preferably a base is used to neutralize the hydrogen halide which is liberated during the reaction. Alkali metal hydroxides, e.g. sodium or potassium hydroxide; hydrides; carbonates or alkoxides of 1 to 3 carbon atoms, inclusive or the like can be used.

After the reaction is completed, the product IV is obtained by conventional procedures, e.g. extraction, chromatography, crystallization, and the like.

In order to obtain the products of formulae IIIB and V, the product of formula IV needs merely to be pyrolyzed at or above its melting point temperature. Usually temperatures of 140° to 200° C. are sufficient. High boiling liquids such as xylene, decaline, or a mineral oil may also be employed to produce a uniform temperature in the reaction vessel. Reduced pressure or a nitrogen atmosphere are generally advantageous in this reaction. If the dialkyl hydroxyamine used to prepare compound IV in the prior reaction, had more than 1 carbon atom in the alkyl groups, compounds of formula V are obtained together with compounds of formula IIIB. The obtained compounds, either IIIB or IIIB and V are isolated and purified by standard procedures such as extracting, chromatography, crystallization and fractional crystallization, and the like.

If compounds of formula VA are desired a compound of formula I is reacted with an unsubstituted or N-monoalkylhydroxyamine in which the alkyl group is of 1 to 3 carbon atoms, inclusive. Under the same conditions as described above the reaction with dialkyl hydroxyamine described above 25° to 100° C. and 1 to 24 hours reaction time, in an organic solvent e.g. dimethylformamide, dimethylsulfoxide, hexamethylphosphoric acid amide or tetrahydrofuran, with an added base such as sodium hydride.

Compounds of formula VI are produced by the usual methods of synthesis of Schiff's bases. Generally a selected compound of formula IIIA is heated with an aldehyde or ketone. In the preferred embodiment of this invention, e.g. solvents such as methanol, ethanol, 1- or 2-propanol, dioxane, tetrahydrofuran, together with acetic acid are employed and the reaction mixture is kept at temperatures of 25° to the reflux temperature of the mixture for 0.5 to 6 hours. If acetic acid is used, the mixture is first neutralized and then extracted with an organic solvent. From the extracts the product VI is obtained and purified by conventional procedures, such as evaporation, crystallization or chromatography.

The following preparations and examples are illustrative of the process and products of the present invention, but are not to be construed as limiting.

Preparation 1

7-Bromo-5-(2-pyridyl)-3H-1,4-benzodiazepin-2-yl hydrazine

A mixture of 7-bromo-1,3-dihydro-5-(2-pyridyl)-2H-1,4-benzodiazepine-2-thione (U.S. Pat. No. 3,734,922) (16.01 g., 10.048 mole), hydrazine hydrate (7.51 g, 0.15 mole) and methanol (400 ml.) was stirred at ambient temperature for 19 hours with a stream of nitrogen bubbling through the mixture. The resulting solid was collected by filtration, washed with methanol and dried to give 13.6 g. of 7-bromo-5-(2-pyridyl)-3H-1,4-benzodiazepin-2-yl hydrazine of melting point 224°–225° C. with decomposition. The analytical sample was recrystallized from methanol-chloroform and had a melting point of 224°–226° C. (dec.).

Anal. calcd. for $C_{14}H_{12}N_4Br$: C, 50.93; H, 3.66; Br, 24.20; N, 21.21. Found: C, 50.77; H, 3.82; Br, 24.22; N, 21.29.

Preparation 2

8-Bromo-1-(chloromethyl)-6-(2-pyridyl)-4H-s-triazolo[4,3-a][1,4]benzodiazepine (I)

7-Bromo-5-(2-pyridyl)-3H-1,4-benzodiazepin-2-yl hydrazine (4.95 g., 0.015 mole) is slowly added to 50 ml. of acetic acid with external cooling. A solution of 1.69 g. of chloroacetyl chloride in 25 ml. of acetic acid is then added during about ten minutes, the solution is stirred at room temperature for about 1.5 hours and 1.23 g. of sodium acetate added with additional stirring for about 30 minutes. The mixture is then refluxed for about 3.25 hours. This mixture is cooled, poured into ice water and concentrated to a small volume, then diluted with water, neutralized with sodium bicarbonate and extracted with chloroform. The extract is dried over anhydrous magnesium sulfate, concentrated, and the residue chromatographed on a column of 250 g. of silica gel, with 5% methanol-95% chloroform. The product obtained from the column is 8-bromo-1-(chloromethyl)-6-(2-pyridyl)-4H-s-triazolo[4,3-a][1,4]benzodiazepine.

Preparation 3

8-Chloro-1-(bromomethyl)-6-(2-pyridyl)-4H-s-triazolo[4,3-a][1,4]benzodiazepine

Following the procedure of Preparation 2, but substituting bromoacetyl bromide for chloroacetyl chloride and using 7-chloro-5-(2-pyridyl)-3H-1,4-benzodiazepine-2-yl hydrazine yields 8-chloro-1-(bromomethyl)-6-(2-pyridyl)-4H-s-triazolo[4,3-a][1,4]benzodiazepine.

Preparation 4

8-Bromo-1-(bromomethyl)-6-(2-pyridyl)-4H-s-triazolo[4,3-a][1,4]benzodiazepine (I)

Following the procedure of Preparation 2, but substituting bromoacetyl bromide for chloroacetyl chloride, yields 8-bromo-1-(bromomethyl)-6-(2-pyridyl)-4H-s-triazolo[4,3-a][1,4]benzodiazepine.

Preparation 5

2-(2-Amino-5-thiocyanobenzoyl)pyridine

A suspension of 2-(2-aminobenzoyl)pyridine [K. Schofield, J. Chem. Soc. 2408 (1949)] (79.2 g., 0.40 mole) and sodium thiocyanate (111.4 g., 1.38 mole) in methanol (300 ml.) was cooled to 0° and treated, dropwise with a cold solution of bromine (81.9 g., 0.51 mole) in methanol (105 ml., saturated with sodium bromide). The resulting mixture was stirred for an additional 1 hour at 0°, allowed to come to ambient temperature and poured into 2 liters of cold water. The mixture was neutralized with a 20% solution of sodium carbonate in water, and extracted with ethyl acetate. The extract was dried over anhydrous sodium sulfate and concentrated in vacuo. The solid residue was dissolved in hot methanol and decolorized with Darco (activated carbon). The resulting solution was diluted with water and allowed to crystallize at about 4° C. to give 78 g. (76.5%) of 2-(2-amino-5-thiocyanobenzoyl)pyridine of melting point 103.5°–105° C. The analytical sample had melting point 102°–103.5° C.

Anal. calcd. for $C_{13}H_9N_3OS$: C, 60.92; H, 3.56; N, 16.46; S, 12.56; Found: C, 61.02; H, 3.81; N, 16.46; S, 12.57.

Preparation 6

2-(2-Amino-5-methylthiobenzoyl)pyridine

A suspension of 2-(2-amino-5-thiocyanobenzoyl)pyridine 0.5 g., (0.002 mole) in ethanol (5 ml.) was warmed to 50° and treated with sodium hydrosulfite (0.56 g., 0.0032 mole) and 10% sodium hydroxide (3.3 ml.), alternately, in portions. The temperature of the mixture was raised to 80° and then cooled to 40°. It was then treated, dropwise, with 0.36 g. (0.0028 mole) of dimethyl sulfate. The mixture was stirred at ambient temperature for 1 hour and concentrated in vacuo to remove ethanol. The resulting mixture was diluted with water and extracted with benzene. The extract was washed with water and brine, dried over anhydrous potassium carbonate and concentrated. The oily residue was chromatographed over silica gel (100 g.) with mixtures of methylene chloride, acetone and Skellysolve B (hexanes) to give 0.25 g. of 2-(2-amino-5-methylthiobenzoyl)pyridine as an oil.

Preparation 7

7-Methylthio-1,3-dihydro-5-(2-pyridyl)-2H-1,4-benzodiazepin-2-one

A stirred solution of 2-[2-amino-5-(methylthio)benzoyl]pyridine (0.0249 mole) in acetic acid (250 ml.) was treated during 5 minutes with 5.02 g. of bromoacetyl bromide. This mixture was kept at ambient temperature for 2 hours and concentrated in vacuo. The residue was carefully treated with about 150 ml. of liquid ammonia. The ammonia was allowed to evaporate and the residue was mixed with water and extracted with methylene chloride. The extract was dried over anhydrous sodium sulfate and concentrated. The residue was crystallized to give 7-methylthio-1,3-dihydro-5-(2-pyridyl)-2H-1,4-benzodiazepin-2-one.

Preparation 8

7-Methylthio-1,3-dihydro-5-(2-pyridyl)-2H-1,4-benzodiazepine-2-thione

A stirred solution of 7-methylthio-1,3-dihydro-5-(2-pyridyl)-2H-1,4-benzodiazepin-2-one (0.0206 mole) in dry pyridine (400 ml.) was treated with phosphorus pentasulfide (5.05 g.), warmed, under nitrogen, at 110–120° C. for 1 hour, cooled and concentrated in vacuo. Residual pyridine was removed by the successive addition of xylene and toluene to the residue with concentration after each addition. The resulting residue was mixed with dilute sodium carbonate and extracted with chloroform. The chloroform extract was washed with brine, dried over anhydrous sodium sulfate and concentrated. The residue was crystallized to give 7-methylthio-1,3-dihydro-5-(2-pyridyl)-2H-1,4-benzodiazepine-2-thione.

Preparation 9

7-Methylthio-5-(2-pyridyl)-3H-1,4-benzodiazepin-2-yl hydrazine

According to the procedure of Preparation 1, 7-methylthio-1,3-dihydro-5-(2-pyridyl)-2H-1,4-benzodiazepine-2-thione is reacted with hydrazine hydrate in methanol to give 7-methylthio-5-(2-pyridyl)-3H-1,4-benzodiazepin-2-yl hydrazine.

Preparation 10

8-Methylthio-1-(chloromethyl)-6-(2-pyridyl)-4H-s-triazolo[4,3-a]1,4]benzodiazepine (I)

According to the procedure of Preparation 2, 7-methylthio-5-(2-pyridyl)-3H-1,4-benzodiazepin-2-yl hydrazine was reacted with chloroacetyl chloride in acetic acid to give 8-methylthio-1-(chloromethyl)-6-(2-pyridyl)-4H-s-triazolo[4,3-a][1,4]benzodiazepine.

EXAMPLE 1

8-Chloro-6-phenyl-1-[(phthalimidooxy)methyl]-4H-s-triazolo[4,3-a][1,4]benzodiazepine A stirred solution of N-hydroxyphthalimide (5.38 g.) and triethylamine (9.15 ml. in dimethylformamide (100 ml.) was treated with 8-chloro-1-(chloromethyl)-6-phenyl-4H-s-triazolo[4,3-a][1,4]benzodiazepine (10.3 g.) and kept at ambient temperature, under nitrogen, for 3 hours 35 minutes. It was poured into cold water, stirred for a few minutes, and filtered. The solid was washed with water and chloroform and dried to give 9.88 g. of 8-chloro-6-phenyl-1-[(phthalimidooxy)methyl]-4H-s-triazolo[4,3-a][1,4]benzodiazepine, melting point 260°–261° C. dec. The filtrate was extracted wtih chloroform. The extract was washed with brine, dried over anhydrous sodium sulfate and concentrated. The residue was mixed with xylene and again concentrated in vacuo to remove residual dimethylformamide. The solid residue was mixed with ethanol and filtered. The solid was washed with ethanol and dried to give 3.02 g. of additional product of melting point 255°–255.5° C. dec. The analytical sample was recrystallized from ethanol-chloroform and had melting point 256.5°–257.5° C. (dec).

Anal. calcd. for $C_{25}H_{16}ClN_5O_3$: C, 63.90; H, 3.43; N, 14.90. Found: C, 63.57; H, 3.67; N, 14.95.

EXAMPLE 2

1-[(Aminooxy)methyl]-8-chloro-6-phenyl-4H-s-triazolo[4,3-a][1,4]benzodiazepine A stirred suspension of 8-chloro-6-phenyl-1-[(phthalimidooxy)methyl]-4H-s-triazolo[4,3-a][1,4]benzodiazepine (9.4 g., 0.02 mole) in absolute ethanol (100 ml.) was treated with hydrazine hydrate (1.45 ml.) and warmed, under nitrogen, at a bath temperature at 70° C. for 3 hours. The mixture was cooled in an ice bath and filtered. The solid was washed with ethanol and methylene chloride. The combined filtrate was concentrated in vacuo; the residue was mixed with water and extracted with methylene chloride. The extract was washed with water, dried over anhydrous sodium sulfate and concentrated. The residue was dissolved in chloroform-ethyl-acetate and filtered through a small pad of silica gel. The filtrate was crystallized from methanol-ethylacetate to give 1-[(aminooxy)methyl]-8-chloro-6-phenyl-4H-s-triazolo[4,3-a][1,4]benzodiazepine in three crops: 1.95 g. of melting point 190°–191.5° C.; 0.89 g. of melting point 183°–186° C.; 0.285 g. of melting point 183°–186° C. The analytical sample had a melting point 191°–192° C.

Anal. calcd. for $C_{17}H_{14}ClN_5O$: C, 60.09; H, 4.15; Cl, 10.43; N, 20.61; Found: C, 59.54; 59.90; H, 4.16; 4.45; Cl, 10.45; N, 20.51; 20.44.

EXAMPLE 3

8-Chloro-6-(o-chlorophenyl)-1-[(phthalimidooxy)methyl]-4H-s-triazolo[4,3-a][1,4]benzodiazepine In the manner given in Example 1, N-hydroxyphthalimide and triethylamine in dimethylacetamide is treated with 8-chloro-6-(o-chlorophenyl)-1-(chloromethyl)-4H-s-triazolo[4,3-a][1,4]benzodiazepine to give 8-chloro-6-(o-chlorophenyl)-1-[(phthalimidooxy)methyl]-4-H-s-triazolo[4,3-a][1,4]benzodiazepine.

EXAMPLE 4

1-[(Aminooxy)methyl]-8-chloro-6-(o-chlorophenyl)-4H-s-triazolo[4,3-a][1,4]benzodiazepine In the manner given in Example 2, a solution of hydrazine hydrate in ethanol is reacted at 65° C. with 8-chloro-6-(o-chlorophenyl)-1-[(phthalimidooxy)methyl]-4H-s-triazolo[4,3-a][1,4]benzodiazepine to give 1-[(aminooxy)methyl]-8-chloro-6-(o-chlorophenyl)-4H-s-triazolo[4,3-a][1,4]benzodiazepine.

EXAMPLE 5

8-Fluoro-6-phenyl-1-[(phthalimidooxy)methyl]-4H-s-triazolo[4,3-a][1,4]benzodiazepine In the manner given in Example 1, N-hydroxyphthalimide and triethylamine in dimethylacetamide is treated with 8-fluoro-6-phenyl-1-(chloromethyl)-4H-s-triazolo[4,3-a][1,4]benzodiazepine to give 8-fluoro-6-phenyl-1-[(phthalimidooxy)methyl]-4H-s-triazolo[4,3-a][1,4]-benzodiazepine.

EXAMPLE 6

1-[(Aminooxy)methyl]-8-fluoro-6-phenyl-4H-s-triazolo[4,3-a][1,4]benzodiazepine

In the manner given in Example 2, solution of hydrazine hydrate in ethanol is reacted at 65° C. with 8-fluoro-1-[(phthalimidooxy)methyl]-6-phenyl-4H-s-triazolo[4,3-a][1,4]benzodiazepine to give 1-(aminooxy)methyl]-8-fluoro-6phenyl-4H-s-triazolo[4,3-a][1,4]-benzodiazepine.

EXAMPLE 7

8-Trifluoromethyl-6-(o-chlorophenyl)-1-[(phthalimidooxy)methyl]-4H-s-triazolo[4,3-a[1,4]-benzodiazepine In the manner given in EXAMPLE 1, N-hydroxyphthalimide and triethylamine in dimethylacetamide is treated with 8-trifluoromethyl-6-(o-chlorophenyl)-1-chloromethyl)-4H-s-triazolo[4,3-a][1,4]benzodiazepine to give 8-trifluoromethyl-6-(o-chlorophenyl)-1-[(phthalimidooxy)methyl]-4H-s-triazolo[4,3-a][1,4]benzodiazepine.

EXAMPLE 8

1-[(Aminooxy)methyl]-8-trifluoromethyl-6-(o-chlorophenyl)-4H-s-triazolo[4,3-a][1,4]benzodiazepine In the manner given in Example 2, a solution of hydrazine hydrate in ethanol is reacted at 65° C. with 8-trifluoromethyl-6-(o-chlorophenyl)-1-[(phthalimidooxy)methyl]-4H-s-triazolo[4,3-a][1,4]benzodiazepine to give 1-[(aminooxy)methyl]-8-trifluoromethyl-6-(o-chlorophenyl)-4H-s-triazolo[4,3-a]1,4]benzodiazepine.

EXAMPLE 9

8-Nitro-6-(o-chlorophenyl)-1-[(phthalimidooxy)methyl]-4H-s-triazolo[4,3-a][1,4]benzodiazepine In the manner given in Example 1, N-hydroxyphthalimide and triethylamine in dimethylacetamide is treated with 8-nitro-6-(o-chlorophenyl)-1-(chloromethyl)-4H-s-triazolo[4,3-a][1,4]benzodiazepine to give 8-nitro-6-(o-chlorophenyl)-1-[(phthalimidooxy)methyl]-4H-s-triazolo][4,3-a][1,4]benzodiazepine.

EXAMPLE 10

1-[(Aminooxy)methyl]-8-nitro-6-(o-chlorophenyl)-4H-s-triazolo[4,3-a][1,4]benzodiazepine In the manner given in Example 2, a solution of hydrazine hydrate in ethanol is reacted at 65° C. with 8-nitro-1-[(phthalimidooxy)methyl]-6-(o-chlorophenyl)-4H-s-triazolo[4,3-a][1,4]benzodiazepine to give 1-[(aminooxy)methyl]-8-nitro-6-(o-chlorophenyl)-4H-s-triazolo[4,3-a][1,4]benzodiazepine.

EXAMPLE 11

8-Methylthio-6phenyl-1-[(phthalimidooxy)methyl]-4H-s-triazolo[4,3-a][1,4]benzodiazepine In the manner given in Example 1, N-hydroxyphthalimide and triethylamine in dimethylformamide is treated with 8-methylthio-6-phenyl-1-(chloromethyl)-4H-s-triazolo[4,3-a][1,4]benzodiazepine to give 8-methylthio-6-phenyl-1-[(phthalimidooxy)methyl]-4H-s-triazolo[4,3-a][1,4]benzodiazepine.

EXAMPLE 12

1-[(Aminooxy)methyl]-8-methylthio-6-phenyl-4H-s-triazolo[4,3-a][1,4]benzodiazepine In the manner given in Example 2, a solution of hydrazine hydrate in ethanol is reacted at 65° C. with 8-methylthio-6-phenyl-1-[(phthalimidooxy)methyl]-4H-s-triazolo[4,3-a][1,4]benzodiazepine to give 1-[(aminooxy)methyl]-8-methylthio-6-phenyl-4H-s-triazolo[4,3-a][1,4]-benzodiazepine.

EXAMPLE 13

8-Bromo-6-(2-pyridyl)-1-[(phthalimidooxy)methyl]-4H-s-triazolo[4,3-a][1,4]benzodiazepine In the manner given in Example 1, N-hydroxyphthalimide and triethylamine in dimethylacetamide is treated with 8-bromo-6-(2-pyridyl)-1-(chloromethyl)-4H-s-triazolo[4,3-a][1,4]benzodiazepine to give 8-bromo-6-(2-pyridyl)-1-[(phthalimidooxy)methyl]-4H-s-triazolo[4,3-a][1,4]benzodiazepine.

EXAMPLE 14

1-[(Aminooxy)methyl]-8-bromo-6-(2-pyridyl)-4H-s-triazolo[4,3-a][1,4]benzodiazepine In the manner given in Example 2, a solution of hydrazine hydrate in ethanol is reated at 65° C. with 8-bromo-1-[(phthalimidooxy)methyl]-6-(2-pyridyl)-4H-s-triazolo[4,3-a][1,4]benzodiazepine to give 1-(aminooxy)methyl]-8-bromo-6-(2pyridyl)-4H-s-triazolo[4,3-a][1,4]benzodiazepine.

In the same manner given in Example 2 combined with Example 1, other 6-phenyl- or respectively 6-(2-pyridyl)-1-[(aminooxy)methyl]-4H-s-triazolo[4,3-a][1,4]benzodiazepines of formula IIIA can be prepared. Representative compounds thus obtained include:

8-bromo-6-phenyl-1-[(aminooxy)methyl]-4H-s-triazolo[4,3-a][1,4]benzodiazepine;
8-chloro-6-(o-fluorophenyl)-1-[(aminooxy)methyl]-4H-s-triazolo[4,3-a][1,4]benzodiazepine;
8-chloro-6-(2,6-difluorophenyl)-1-[(aminooxy)methyl]-4H-s-triazolo[4,3-a][1,4]benzodiazepine;
6-(o-chlorophenyl)-1-[(aminooxy)methyl]-4H-s-triazolo[4,3-a][1,4]benzodiazepine;
6-(o-fluorophenyl)-1-[(aminooxy)methyl]-4H-s-triazolo[4,3-a][1,4]benzodiazepine;
8-nitro-6-phenyl-1-[(aminooxy)methyl]-4H-s-triazolo[4,3-a][1,4]benzodiazepine;
8-bromo-6-(o-chlorophenyl)-1-[(aminooxy)methyl]-4H-s-triazolo[4,3-a][1,4]benzodiazepine;
8-trifluoromethyl-6-phenyl-1-[(aminooxy)methyl]-4H-s-triazolo[4,3-a][1,4]benzodiazepine;
8-fluoro-6-(o-chlorophenyl)-1-[(aminooxy)methyl]-4H-s-triazolo[4,3-a][1,4]benzodiazepine;
8-fluoro-6-o-fluorophenyl)-1-[(aminooxy)methyl]-4H-s-triazolo[4,3-a][1,4]benzodiazepine;
7-chloro-6-(o-chlorophenyl)-1-[(aminooxy)methyl]-4H-s-triazolo[4,3-a][1,4]benzodiazepine;
9-bromo-6-phenyl-1-[(aminooxy)methyl]-4H-s-triazolo[4,3-a][1,4]benzodiazepine;
10-nitro-6-(o-fluorophenyl)-1-[(aminooxy)methyl]-4H-s-triazolo[4,3-a][1,4]benzodiazepine;
9-trifluoromethyl-6-(o-chlorophenyl)-1-[(aminooxy)methyl]-4H-s-triazolo[4,3-a][1,4]benzodiazepine;

8-chloro-6-(2-pyridyl)-1-[(aminooxy)methyl]-4H-s-triazolo[4,3-a][1,4]benzodiazepine;
8-fluoro-6-(2-pyridyl)-1-[(aminooxy)methyl]-4H-s-triazolo-[4,3-a][1,4]benzodiazepine;
8-nitro-6-(2-pyridyl)-1-(aminooxy)methyl]-4H-s-triazolo-[4,3-a][1,4]benzodiazepine;
8-trifluoromethyl-6-(2-pyridyl)-1-[(aminooxy)methyl]-4H-s-triazolo[4,3-a][1,4]benzodiazepine;
7-nitro-6-(2-pyridyl)-1-[(aminooxy)methyl]-4H-s-trizaolo-[4,3-a][1,4]benzodiazepine;
9-bromo-6-(2-pyridyl)-1-[(aminooxy)methyl]-4H-s-triazolo-[4,3-a][1,4]benzodiazepine;
10-chloro-6-(2-pyridyl)-1-[(aminooxy)methyl]-4H-s-triazolo[4,3-a][1,4]benzodiazepine;
8-ethylthio-6-(2-pyridyl)-1-[(aminooxy)methyl]-4H-s-triazolo[4,3-a][1,4]benzodiazepine;
8-propylthio-6-(o-chlorophenyl)-1-[(aminooxy)methyl]-4H-s-triazolo[4,3-a][1,4]benzodiazepine;
8-isopropylthio-6-(2,6-difluorophenyl)-1-[(aminooxy)-methyl]-4H-s-triazolo[4,3-a][1,4]benzodiazepine;
8-methylthio-6-(o-chlorophenyl)-1-(aminooxy)methyl]-4H-s-triazolo[4,3-a][1,4]benzodiazepine;
6-phenyl-1-[(aminooxy)methyl]-4H-s-triazolo[4,3-a][1,4]-benzodiazepine;
8-methylthio-6-(2-pyridyl)-1-[(aminooxy)methyl]-4H-s-triazolo[4,3-a][1,4]benzodiazepine; and the like.

EXAMPLE 15

8-Chloro-1-[(dimethylamino)methyl]-6-phenyl-4H-s-triazolo[4,3-a][1,4]benzodiazepine, $N^1$-oxide, hydrate A stirred solution of N,N-dimethylhydroxylamine (3.67 g., 0.06 mole) in dry dimethylformamide (50 ml. is cooled in an ice bath, under nitrogen, and treated with a 57% mineral oil suspension of sodium hydride (0.84 g., 0.02 mole). The mixture of kept at ambient temperature for 1 hour (a precipitate formed) and then cooled in an ice bath and treated with 8-chloro-1-(chloromethyl)-6-phenyl-4H-s-triazolo[4,3-a][1,4]benzodiazepine (6.86 g., 0.02 mole). The mixture is kept at ambient temperature for 2 hours and concentrated in vacuo. Last traces of dimethylformamide are removed from the residue by the successive addition and distillation of xylene, toluene, and benzene. The resulting material is chromatographed on silica gel (250 g.) with methanol. The product thus obtained is crystallized from methanol-ethyl acetate following activated charcoal treatment) to give 8-chloro-1-[(dimethylamino)methyl]-6-phenyl-4H-s-triazolo[4,3-a][1,4]benzodiazepine, $N^1$-oxide, hydrate in three crops: 3.377 g. of melting point 160.5°–162.5° C.; 1.145 g. of melting point 160°–162° C.; and 0.785 g. of melting point 160°–162° C. The analytical sample had a melting point of 157.5°–158.5° C. with decomposition.

Anal. calcd. for $C_{19}H_{18}ClN_5O$: C, 62.04, H, 4.93; Cl, 9.64; N, 19.04. Found: C, 59.89; H, 5.15; Cl, 8.69; 9.35; N, 18.77; $H_2O$, 3.22. Anal. calcd. for 3.22% $H_2O$; C, 61.88; H, 4.96; Cl, 8.98; 9.66; H, 19.39.

EXAMPLE 16

8-Chloro-1-[(diethylamino)methyl]-6-phenyl-4H-s-triazolo[4,3-a][1,4]benzodiazepine, $N^1$-oxide, hydrate A stirred, ice cold solution of N,N-diethylhydroxylamine (50 ml.). in dimethylformamide (50 ml.) under nitrogen, was treated with a 57% suspension of sodium hydride in mineral oil (1.39 g., 0.033 mole). The mixture was kept at ambient temperature for 55 minutes, cooled in an ice bath and treated with 8-chloro-1-(chloromethyl)-6-phenyl-4H-s-triazolo[4,3-a][1,4]benzodiazepine (10.3 g., 0.03 mole). This mixture was kept at ambient temperature for 18 hours and poured into ice water. The resulting mixture was saturated with sodium chloride and extracted with chloroform. The extract was washed with brine, dried over anhydrous sodium sulfate and concentrated. The residue was mixed with xylene and concentrated in vacuo, the resulting material was crystallized from wet methanol-ethyl acetate to give 8-chloro-1-[(diethylamino)methyl]-6-phenyl-4H-s-triazolo[4,3-a][1,4]benzodiazepine, $N^1$-oxide dihydrate in two crops: 5.91 g., of melting point 137°–139.5° C. dec. and 1.16 g., of melting point 135°–137.5° C. The analytical sample had a melting point of 135°–137.5° C. dec.

Anal. calcd. for $C_{21}H_{26}ClN_5O_3$: C, 58.40; H, 6.07; Cl, 8.21; N, 16.22; $H_2O$, 8.34. Found: C, 58.22; H, 6.00; Cl, 8.17; N, 16.28; $H_2O$, 7.86.

EXAMPLE 17

8-Methylthio-1-[(dimethylamino)methyl]-6-phenyl-4H-s-triazolo[4,3-a][1,4]benzodiazepine, $N^1$-oxide In the manner given in Example 15, 8-methylthio-1-(chloromethyl)-6-phenyl-4H-s-triazolo[4,3-a][1,4]benzodiazepine is treated with a cold mixture of N,N-dimethyl-hydroxylamine and sodium hydride in dimethylformamide to give 8-methylthio-1-[(dimethylamino)methyl]-6-phenyl-4H-s-triazolo[4,3-a][1,4]benzodiazepine, $N^1$-oxide.

EXAMPLE 18

8-Chloro-1-[(diethylamino)methyl]-6-(o-chlorophenyl)-4H-s-triazolo[4,3-][1,4]benzodiazapine $N^1$-oxide In the manner given in Example 15, 8-chloro-1-(chloromethyl)-6-(o-chlorophenyl)-4H-s-triazolo[4,3-a]-[1,4-benzodiazepine is treated with a cold mixture of N,N-diethylhydroxylamine and sodium hydride in dimethylformamide to give 8-chloro-1-[(diethylamino)-methyl]-6-(o-chlorophenyl)-4H-s-triazolo[4,3-a][1,4]benzodiazepine $N^1$-oxide.

EXAMPLE 19

8-Chloro-1-[(dimethylamino)methyl]-6-(o-chlorophenyl)-4H-s-triazolo[4,3-a][1,4]benzodiazepine $N^1$-oxide In the manner given in Example 16, a solution of N,N-dimethylhydroxylamine in dimethylformamide is treated with sodium hydride suspended in mineral oil, and the mixture is treated with 8-chloro-1-(bromomethyl)-6-(o-chlorophenyl)-4H-s-triazolo[4,3-a][1,4]benzodiazepine to give 8-chloro-1-[(dimethylamino)methyl]-6-(o-chlorophenyl)-4H-s-triazolo[4,3-a][1,4]benzodiazepine $N^1$-oxide.

EXAMPLE 20

8-Fluoro-1-[(ethylmethylamino)methyl]-6-phenyl-4H-s-triazolo[4,3-a][1,4]benzodiazepine $N^1$-oxide In the manner given in Example 15, 8-fluoro-1-(chloromethyl)-6-phenyl-4H-s-triazolo[4,3-a][1,4]benzodiazepine is treated with a cold mixture of N-ethyl-N-methylhydroxyamine and sodium hydride in dimethylformamide to give 8-fluoro-1-[(ethylmethylamino)methyl]-6-phenyl-4H-s-triazolo[4,3-a][1,4]benzodiazepine $N^1$-oxide.

EXAMPLE 21

8-Fluoro-1-[(dimethylamino)methyl]-6-phenyl-4H-s-triazolo[4,3-a][1,4]benzodiazepine N¹-oxide In the manner given in Example 16, a solution of N,N-dimethylhydroxylamine in dimethylformamide is treated with sodium hydride suspended in mineral oil, and the mixture is treated with 8-fluoro-1-(bromomethyl)6-phenyl-4H-s-triazolo[4,3-a][1,4]benzodiazepine to give 8-fluoro-1-[(dimethylamino)methyl]-6-phenyl-4H-s-triazolo[4,3-a][1,4]benzodiazepine, N¹-oxide.

EXAMPLE 22

8-Trifluoromethyl-1-[(diethylamino)methyl]-6-phenyl-4H-s-triazolo[4,3-a][1,4]benzodiazepine N¹-oxide In the manner given in Example 15, 8-trifluoromethyl-1-(chloromethyl)6-phenyl-4H-s-triazolo[4,3-a][1,4]-benzodiazepine is treated with a cold mixture of N,N-diethylhydroxylamine and sodium hydride in dimethylformamide to give 8 trifluoromethyl-1-[(diethylamino)methyl]-6-phenyl-4H-s-triazolo[4,3-a][1,4]benzodiazepine N¹-oxide.

EXAMPLE 23

8Nitro-1-[(dimethylamino)methyl]-6-(o-chlorophenyl)-4H-s-triazolo[4,3-a][1,4]benzodiazepine, N¹-oxide In the manner given in Example 16, a solution of N,N-dimethylhydroxylamine in dimethylformamide is treated with sodium hydride, suspended in mineral oil, and the mixture is treated with 8-nitro-1-(chloromethyl)-6-(o-chlorophenyl)-4H-s-triazolo[4,3-a][1,4]benzodiazepine to give 8-nitro-1-[(dimethylamino)methyl]-6-(o-chlorophenyl)-4H-s-triazolo[4,3-a][1,4]benzodiazepine, N¹-oxide.

EXAMPLE 24

8-Nitro-1-[(dipropylamino)methyl]-6-(o-chlorophenyl)-4H-s-triazolo[4,3-a][1,4]benzodiazepine, N¹-oxide In the manner given in Example 15, 8-nitro-1-(chloromethyl)-6-(o-chlorophenyl)-4H-s-triazolo[4,3-a][1,4]benzodiazepine is treated with a cold mixture of N,N-dipropylhydroxylamine and sodium hydride in dimethyl-formamide to give 8-nitro-1-[(dipropylamino)methyl]-6-(o-chlorophenyl)-4H-s-triazolo[4,3-a][1,4]benzodiazepine, N¹-oxide.

EXAMPLE 25

8-Nitro-1-[(diisopropylamino)methyl]-6-(o-chlorophenyl)-4H-s-triazolo[4,3-a][1,4]benzodiazepine, N¹-oxide.

In the manner given in Example 16, a solution of N,N-diisopropylhydroxylamine in dimethylformamide is treated with sodium hydride suspended in mineral oil, and the mixture is treated with 8-nitro-1-(chloromethyl)-6-(o-chlorophenyl)-4H-s-triazolo[4,3-a][1,4-benzodiazepine to give 8-nitro-1-[(diisopropylamino)methyl]-6-(o-chlorophenyl)-4H-s-triazolo[4,3-a][1,4]benzodiazepine, N¹-oxide.

EXAMPLE 26

8-Bromo-1-[(diethylamino)methyl]-6-(2-pyridyl)-4H-s-triazolo[4,3-a][1,4]benzodiazepine, N¹-oxide In the manner given in Example 15, 8-bromo-1-(chloromethyl)-6-(2-pyridyl)-4H-s-triazolo[4,3-a][1,4]-benzodiazepine is treated with a cold mixture of N,N-diethylhydroxylamine and sodium hydride in dimethylformamide to give 8-bromo-1-[(diethylamino)methyl]-6-(2-pyridyl)-4H-s-triazolo[4,3-a][1,4]benzodiazepine, N¹-oxide.

EXAMPLE 27

8-Bromo-1-[(dimethylamino)methyl]-6-(2-pyridyl)-4H-s-triazolo[4,3-a][1,4]benzodiazepine, N¹-oxide.

In the manner given in Example 16, a solution of N,N-dimethylhydroxylamine in dimethylformamide is treated with sodium hydride suspended in mineral oil, and the mixture is treated with 8-bromo-1-(chloromethyl)-6-(2-pyridyl)-4H-s--triazolo[4,3-a][1,4]benzodiazepine to give 8-bromo-1-[(dimethylamino)methyl]-6-(2-pyridyl)-4H-s-triazolo[4,3-a][1,4]benzodiazepine, N¹-oxide.

EXAMPLE 28

8-Bromo-1-[(diethylamino)methyl]-6-(o-chlorophenyl)-4H-s-triazolo[4,3-a][1,4]benzodiazepine, N¹-oxide In the manner given in Example 15, 8-bromo-1-(chloromethyl)-6-(o-chlorophenyl)-4H-s-triazolo[4,3-a][1,4]benzodiazepine is treated with a cold mixture of N,N-diethylhydroxylamine and sodium hydride in dimethylformamide to give 8-bromo-1-[(diethylamino)methyl]-6-(o-chlorophenyl)-4H-s-triazolo[4,3-a][1,4]benzodiazepine, N¹-oxide.

EXAMPLE 29

8-Bromo-1-[(methylpropylamino)methyl]-6-(o-chlorophenyl)-4H-s-triazolo[4,3-a][1,4]benzodiazepine, N¹-oxide.

In the manner given in Example 16, a solution of N-methyl-N-propylhydroxylamine in dimethylformamide is treated with sodium hydride suspended in mineral oil and the mixture is treated with 8-chloro-1-(bromomethyl)-6-(o-chlorophenyl)-4H-s-triazolo[4,3-a][1,4]benzodiazepine to give 8-bromo-1-[(methylpropylamino)methyl]-6-(o-chlorophenyl)-4H-s-triazolo[4,3-a][1,4]benzodiazepine.

EXAMPLE 30

8-Bromo-1-[(methylhydroxyamino)methyl]-6-(2-pyridyl)-4H-s-triazolo[4,3-a][1,4]benzodiazepine In the manner given in Example 16, a solution of N-methylhydroxylamine in dimethylformamide is treated with sodium hydride suspended in mineral oil, and the mixture is treated with 8-bromo-1-(chloromethyl)-6-(2-pyridyl)-4H-s-triazolo[4,3-a][1,4]benzodiazepine to give 8-bromo-1-[(methylhydroxyamino)methyl]-6-(2-pyridyl)4H-s-triazolo[4,3-a][1,4]benzodiazepine.

EXAMPLE 31

8-Chloro-1-[(hydroxyamino)methyl]-6-phenyl-4H-s-triazolo[4,3-a][1,4]benzodiazepine In the manner given in Example 15, 8-chloro-1-(chloromethyl)-6-phenyl-4H-s-triazolo[4,3-a][1,4]-benzodiazepine is treated with a cold mixture of hydroxylamine and sodium hydride in dimethylformamide to give 8-chloro-1-[(hydroxyamino)methyl]-6-phenyl-4H-s-triazolo[4,3-a][1,4]benzodiazepine.

EXAMPLE 32

8-Bromo-1-[(ethylhydroxyamino)methyl]-6-(2-pyridyl)-4H-s-triazolo[4,3-a][1,4]benzodiazepine In the manner given in Example 16, a solution of N-ethylhydroxylamine in dimethylformamide is treated with sodium hydride suspended in mineral oil, and the mixture is treated with 8-bromo-1-(chloromethyl)-6-(2-pyridyl)-4H-s-triazolo[4,3-a][1,4]benzodiazepine to give 8-bromo-1-[(ethylhydroxyamino)methyl]-6-(2-pyridyl)-4H-s-triazolo[4,3-a][1,4]benzodiazepine.

EXAMPLE 33

8-Chloro-1-[(hydroxyamino)methyl]-6-(o-chlorophenyl)-4H-s-triazolo[4,3-a][1,4]benzodiazepine In the manner given in Example 15, 8-chloro-1-(chloromethyl)-6-(o-chlorophenyl)-4H-s-triazolo[4,3-a][1,4]benzodiazepine is treated with a cold mixture of hydroxylamine and sodium hydride in dimethylformamide to give 8-chloro-1-[(hydroxyamino)methyl]-6-(o-chlorophenyl)-4H-s-triazolo[4,3-a][1,4]benzodiazepine.

In the manner given in the prior Examples 15 through 29, other 1-[(dialkylamino methyl]-6-phenyl-or 6-(2-pyridyl)-4H-s-triazolo[4,3-a][1,4]benzodiazepine $N^1$-oxides can be synthesized. Representative compounds, thus obtained include:

8-bromo-6-(2,6-difluorophenyl)-1-(dimethylamino)methyl]-4H-s-triazolo[4,3-a][1,4]benzodiazepine $N^1$-oxide;
8-chloro-6-(o-fluorophenyl)-1-[(methylethylamino)methyl]-4H-s-triazolo[4,3-a][1,4]benzodiazepine $N^1$-oxide;
8-chloro-6-(2,6-difluorophenyl)-1-[(dimethylamino)methyl]-4H-s-triazolo[4,3-a][1,4]benzodiazepine $N^1$-oxide;
6-(o-chlorophenyl)-1-[(dimethylamino)methyl]-4H-s-triazolo[4,3-a][1,4]benzodiazepine $N^1$-oxide;
6-(o-fluorophenyl)-1-[(methylisopropylamino)methyl[-4H-s-triazolo[4,3-a][1,4]benzodiazepine $N^1$-oxide;
8-nitro-6-phenyl-1-[(dimethylamino)methyl]-4-s-triazolo[4,3-a][1,4]benzodiazepine $N^1$-oxide;
8-bromo-6-(o-chlorophenyl)-1-[(ethylpropylamino)methyl]-4H-s-triazolo[4,3-a][1,4]benzodiazepine $N^1$-oxide;
8-trifluoromethyl-6-phenyl-1-[(diethylamino)methyl[-4H-s-triazolo[4,3-a][1,4]benzodiazepine $N^1$-oxide;
8-fluoro-6-(o-chlorophenyl)-1-[(methylethylamino)methyl]-4H-s-triazolo[4,3-a][1,4]benzodiazepine $N^1$-oxide;
8-fluoro-6-(o-fluorophenyl)-1-[(dimethylamino)methyl]-4H-s-triazolo[4,3-a][1,4]benzodiazepine $N^1$-oxide;
7-chloro-6-(o-chlorophenyl)-1-[(dipropylamino)methyl]-4H-s-triazolo[4,3-a][1,4]benzodiazepine $N^1$-oxide;
9-bromo-6-phenyl-1-phenyl-1-[(dipropylamino)methyl]-4H-s-triazolo-[4,3-a][1,4]benzodiazepine $N^1$-oxide;
10-nitro-6-(o-fluorophenyl)-1-[(dimethylamino)methyl]-4H-s-triazolo[4,3-a][1,4]benzodiazepine $N^1$-oxide;
9-trifluoromethyl-6-(o-chlorophenyl)-1-[(diisopropylamino)-methyl]-4H-s-triazolo[4,3-a][1,4]benzodiazepine $N^1$-oxide;
8-chloro-6-(2-pyridyl)-1-[(methylpropylamino)methyl]-4H-s-triazolo[4,3-a][1,4]benzodiazepine $N^1$-oxide;
8-fluoro-6-(2-pyridyl)-1-[(methylisopropylamino)methyl]-4H-s-triazolo[4,3-a][1,4]benzodiazepine $N^1$-oxide;
8-nitro-6-(2-pyridyl)-1-[(dipropylamino)methyl]-4H-s-triazolo[4,3-a][1,4]benzodiazepine $N^1$-oxide;
8-trifluoromethyl-6-(2-pyridyl)-1-[(diisopropylamino)-methyl]-4H-s-triazolo[4,3-a][1,4]benzodiazepine $N^1$-oxide;
7-nitro-6-(2-pyridyl)-1-[(dipropylamino)methyl]-4H-s-triazolo[4,3-a][1,4]benzodiazepine, $N^1$-oxide;
9-bromo-6-(2-pyridyl)-1-[(diisopropylamino)methyl[-4H-s-triazolo[4,3-a][1,4]benzodiazepine, $N^1$-oxide;
10-chloro-6-(2-pyridyl)-1-[(diisopropylamino)methyl[-4H-s-triazolo[4,3-a][1,4]benzodiazepine $N^1$-oxide;
8-ethylthio-6-(2-pyridyl)-1-[(dimethylamino)methyl]-4H-s-triazolo[4,3-a][1,4]benzodiazepine $N^1$-oxide;
8-propylthio-6-(o-chlorophenyl)-1-[(diethylamino)methyl]-4H-s-triazolo[4,3-a][1,4]benzodiazepine $N^1$-oxide;
8-isopropylthio-6-(2,6-difluorophenyl)-1-[(methylethylamino)methyl]-4H-s-triazolo[4,3-a][1,4]benzodiazepine $N^1$-oxide;
1-[(dimethylamino)methyl]-6-phenyl-4H-s-triazolo[4,3-a]-[1,4]benzodiazepine $N^1$-oxide;
8-methylthio-6-(2-pyridyl)-1-[(diethylamino)methyl]-4H-s-triazolo[4,3-a][1,4]benzodiazepine $N^1$-oxide;

In the manner given in the prior Examples 30 through 33, other 1-[(hydroxyamino)methyl]-6-phenyl- or 6-(2-pyridyl)-4H-s-triazolo[4,3-a][1,4]benzodiazepines can be synthesized. Representative compounds, thus obtained, include:

8-bromo-6-(2,6-difluorophenyl)-1-[(methylhydroxyamino)-methyl-4H-s-triazolo[4,3-a][1,4]benzodiazepine;
8-chloro-6-(o-fluorophenyl)-1-[(methylhydroxyamino)-methyl]-4H-s-triazolo[4,3-a][1,4]benzodiazepine;
8-chloro-6-(2,6-difluorophenyl)-1-[(hydroxyamino)-methyl]-4H-s-triazolo[4,3-a][1,4]benzodiazepine;
1-[(methylhydroxyamino)methyl]-4H-s-triazolo[4,3-a]-[1,4]-benzodiazepine;
6-(o-fluorophenyl)-1-[(ethylhydroxyamino)methyl]-4H-s-triazolo[4,3-a][1,4]benzodiazepine;
8-nitro-6-phenyl-1-[(propylhydroxyamino)methyl]-4H-s-triazolo[4,3-a][1,4]benzodiazepine;
8-bromo-6-(o-chlorophenyl)-1-[(isopropylhydroxyamino)-methyl]-4H-s-triazolo[4,3-a][1,4]benzodiazepine;
8-trifluoromethyl-6-phenyl-1-[(hydroxyamino)methyl]-4H-s-triazolo[4,3-a][1,4]benzodiazepine;
8-fluoro-6-(o-chlorophenyl)-1-[(methylhydroxyamino)-methyl]-4H-s-triazolo[4,3-a][1,4]benzodiazepine;
8-fluoro-6-(o-fluorophenyl)-1-[(methylhydroxyamino)-methyl]-4H-s-triazolo[4,3-a][1,4]benzodiazepine;
8-chloro-6-(o-chlorophenyl)-1-[(ethylhydroxyamino)-methyl]-4H-s-triazolo[4,3-a][1,4]benzodiazepine;
9-bromo-6-phenyl-1-[(propylhydroxyamino)methyl]-4H-s-triazolo[4,3-a][1,4]benzodiazepine;
10-nitro-6-(o-fluorophenyl)-1-[(methylhydroxyamino)-methyl]-4H-s-triazolo[4,3-a][1,4]benzodiazepine;

9-trifluoromethyl-6-(o-chlorophenyl)-1-[(isopropylhydroxyamino)methyl]-4H-s-triazolo[4,3-a][1,4]benzodiazepine;
6-(2-pyridyl)-1-[(methylhydroxyamino)methyl]-4H-s-triazolo[4,3-a][1,4]benzodiazepine;
8-nitro-6-(2-pyridyl)-1-[(ethylhydroxyamino)methyl]-4H-s-triazolo[4,3-a][1,4]benzodiazepine;
8-bromo-6-(2-pyridyl)-1-[(isopropylhydroxyamino)methyl]-4H-s-triazolo[4,3-a][1,4]benzodiazepine;
8-trifluoromethyl-6-(2-pyridyl)-1-[(propylhydroxyamino)-methyl[-4H-s-triazolo[4,3-a][1,4]benzodiazepine;
8-fluoro-6-(2-pyridyl)-1-[(methylhydroxyamino)methyl]-4H-s-triazolo[4,3-a][1,4]benzodiazepine;
8-fluoro-6-(2-pyridyl)-1-[(ethylhydroxyamino)methyl]-4H-s-triazolo[4,3-a][1,4]benzodiazepine;
7-chloro-6-(2-pyridyl)-1-[(isopropylhydroxyamino)methyl]-4H-s-triazolo[4,3-a][1,4]benzodiazepine;
9-bromo-6-(2-pyridyl)-1-[(hydroxyamino)methyl]-4H-s-triazolo[4,3-a][1,4]benzodiazepine;
8-methylthio-6-phenyl-1-[(methylhydroxyamino)methyl]-4H-s-triazolo[4,3-a][1,4]benzodiazepine;
8-ethylthio-6-(o-chlorophenyl)-1-[(ethylhydroxyamino)-methyl]-4H-s-triazolo[4,3-a][1,4]benzodiazepine;
8-propylthio-6-(2-pyridyl)-1-[(hydroxyamino)methyl]-4H-s-triazolo[4,3-a][1,4]benzodiazepine; and the like.

EXAMPLE 34

8-Chloro-1-[[(diethylamino)oxy]methyl]-6-phenyl-4H-s-triazolo[4,3-a][1,4]benzodiazepine and
8-chloro-1-[(ethylhydroxyamino)methyl]-6-phenyl-4H-s-triazolo[4,3-a][1,4]benzodiazepine A sample of 8-chloro-1-[(diethylamino)methyl]-6-phenyl-4H-s-triazolo[4,3-a][1,4]benzodiazepine $N^1$-oxide hydrate (4.0 g.), was warmed in an oil bath under reduced pressure (23 mmHg). The temperature of the bath was raised from 112° to 151° C. during 21 minutes and kept at 143°-151° C. for an additional 22 minutes. During this period the solid melted with bubbling. The amber melt was cooled and chromatographed on silica gel (200 g.) with 3% methanol-chloroform. The first compound eluted from the column was crystallized from ethyl acetate-Skellysolve B Hexanes to give 1.89 g., of 8-chloro-1-[[(diethylamino)oxy]methyl]-6-phenyl-4H-s-triazolo[4,3-a][1,4]benzodiazepine of melting point 136°-138.5° C. The analytical sample had melting point 136°-139°.

Anal. calcd. for $C_{21}H_{22}ClN_5O$: C, 63.71; H, 5.60; Cl, 8.95; N, 17.69. Found: C, 64.01; H, 5.91; Cl, 8.89; N, 17.62.

The second compound eluted from the column was crystallized from wet ethyl acetate-Skellysolve B hexanes to give 8-chloro-1-[(ethylhydroxyamino)methyl]-6-phenyl-4H-s-triazolo[4,3-a][1,4]benzodiazepine in three crops: 0.627 g. of melting point 154.5°-157° C.; 0.387 g. of melting point 152°-153.5° C. and 0.141 g. of melting point 150°-153.5° C. The analytical sample was crystallized once from wet ethyl acetate-Skellysolve B hexanes and once from methanol-ethyl acetate and had melting point 199°-200.5° C.

Anal. calcd. for $C_{19}H_{18}ClN_5O$: C, 62.04; H, 4.93; Cl, 9.64; N, 19.04; Found: C, 61.95; H, 5.20; Cl, 9.51; N, 18.86.

EXAMPLE 35

8-Chloro-1-[[(diethylamino)oxy]methyl]-6-(o-chlorophenyl)-4H-s-triazolo[4,3-a][1,4]benzodiazepine and
8-chloro-1-[(ethylhydroxyamino)methyl]-6-(o-chlorophenyl)-4H-s-triazolo[4,3-a][1,4]benzodiazepine In the manner given in Example 34, 8-chloro-1-[(diethylamino)methyl]-6-(o-chlorophenyl)-4H-s-triazolo[4,3-a][1,4]benzodiazepine $N^1$-oxide is heated between 140°-155° C. to give 8-chloro-1-[[(diethylamino)oxy]methyl]-6-(o-chlorophenyl)-4H-s-triazolo[4,3-a][1,4]-benzodiazepine and 8-chloro-[(ethylhydroxyamino)methyl]-6-(o-chlorophenyl)-4H-s-triazolo[4,3-a][1,4]benzodiazepine which are separated from each other by chromatography as in Example 34.

EXAMPLE 36

8-Fluoro-1-[[(ethylmethylamino)oxy]methyl]-6-phenyl-4H-s-triazolo[4,3-a][1,4]benzodiazepine and
8-fluoro-1-[(methylhydroxyamino)methyl]-6-phenyl-4H-s-triazolo[4,3-a][1,4]benzodiazepine In the manner given in Example 34, 8-fluoro-1-[(ethylmethylamino)methyl]-6-phenyl-4H-s-triazolo[4,3-a]-[1,4]benzodiazepine $N^1$-oxide is heated between 140°-155° C. to give 8-fluoro-1-[[(ethylmethylamino)oxy]methyl]-6-phenyl-4H-s-triazolo[4,3-a][1,4]benzodiazepine and 8-fluoro-1-[(methylhydroxyamino)methyl]-6-phenyl-4H-s-triazolo[4,3-a][1,4]benzodiazepine which are separated from each other by chromatography as in Example 34.

EXAMPLE 37

8-Trifluoromethyl-1-[[(diethylamino)oxy]-methyl]-6-(o-chlorophenyl)-4H-s-triazolo[4,3-a][1,4]-benzodiazepine and
8-trifluoromethyl-1-[(ethylhydroxyamino)methyl]-6-(o-chlorophenyl)-4H-s-triazolo[4,3-a][1,4]benzodiazepine In the manner given in Example 34, 8-trifluoromethyl-1-[(diethylamino)methyl]-6-(o-chlorophenyl)-4H-s-triazolo[4,3-a][1,4]benzodiazepine $N^1$-oxide is heated between 140°-155° C. to give 8-trifluoromethyl-1-[[(diethylamino)oxy]methyl]-6-(o-chlorophenyl)-4H-s-triazolo[4,3-a]-[1,4]benzodiazepine and 8-trifluoromethyl-1-[(ethylhydroxyamino)methyl]-6-(o-chlorophenyl)-4H-s-triazolo[4,3-a][1,4]benzodiazepine which are separated from each other by chromatography as in Example 34.

EXAMPLE 38

8-Nitro-1-[[(diethylamino)oxy]methyl]-6-(o-chlorophenyl)-4H-s-triazolo[4,3-a][1,4]benzodiazepine and
8-nitro-1-[(ethylhydroxyamino)methyl]-6-(o-chlorophenyl)-4H-s-triazolo[4,3-a][1,4]benzodiazepine.

In the manner given in Example 34, 8-nitro-1-[(diethylamino)methyl]-6-(o-chlorophenyl)-4H-s-triazolo[4,3-a][1,4]benzodiazepine $N^1$-oxide is heated between 140°-155° C. to give 8-nitro-1-[[(diethylamino)oxy]methyl]-6-(o-chlorophenyl)-4H-s-triazolo[4,3-a][1,4]benzodiazepine and 8-nitro-1-[(ethylhydroxyamino)methyl]-6-(o-chlorophenyl)-4H-s-triazolo[4,3-a][1,4]benzodiazepine which are separated from each other by chromatography as in Example 34.

EXAMPLE 39

8-Bromo-1-[[(ethylmethylamino)oxy]methyl]-6-(2-pyridyl)-4H-s-triazolo[4,3-a][1,4]benzodiazepine and 8-bromo-1-[(methylhydroxyamino)methyl]-6-(2-pyridyl)-4H-s-triazolo[4,3-a][1,4]benzodiazepine;

In the manner given in Example 34, 8-bromo-1-[(ethylmethylamino)methyl]-6-(2-pyridyl)-4H-s-triazolo[4,3-a][1,4]benzodiazepine $N^1$-oxide is heated between 140°–155° C. to give 8-bromo-1-[[(ethylmethylamino)oxy]-methyl]-6-(2-pyridyl)-4H-s-triazolo[4,3-a][1,4]benzodiazepine and 8-bromo-1-[(methylhydroxyamino)methyl]-6-(2-pyridyl)-4H-s-triazolo[4,3-a][1,4]benzodiazepine which are separated from each other by chromatography as in Example 34.

EXAMPLE 40

8-Chloro-1-[[(dipropylamino oxy]methyl]-6-(o-chlorophenyl)-4H-s-triazolo[4,3-a][1,4]benzodiazepine and 8-chloro-1-[(propylhydroxyamino)methyl]-6-(o-chlorophenyl)-4H-s-triazolo[4,3-a][1,4]benzodiazepine In the manner given in Example 34, 8-chloro-1-[(dipropylamino)methyl]-6-(o-chlorophenyl)-4H-s-triazolo[4,3-a][1,4]benzodiazepine $N^1$-oxide is heated between 140°–155° C. to give 8-chloro-1-[[(dipropylamino)oxy]-methyl]-6-(o-chlorophenyl)-4H-s-triazolo[4,3-a][1,4]-benzodiazepine and 8-chloro-1-[(propylhydroxyamino)-methyl]-6-(o-chlorophenyl)-4H-s-triazolo[4,3-a][1,4]-benzodiazepine which are separated from each other by chromatography as in Example 34.

EXAMPLE 41

8-Chloro-1-[[(isopropylmethylamino)oxy]-methyl]-6-phenyl-4H-s-triazolo[4,3-a][1,4]benzodiazepine and 8-chloro-1-[(methylhydroxyamino)methyl]-6-phenyl-4H-s-triazolo[4,3-a][1,4]benzodiazepine In the manner given in Example 34, 8-chloro-1-[(isopropylmethylamino)methyl]-6-phenyl-4H-s-triazolo-[4,3-a][1,4]benzodiazepine $N^1$-oxide is heated between 140°–155° C. to give 8-chloro-1-[[(isopropylmethylamino)oxy]methyl]-6-phenyl-4H-s-triazolo[4,3-a][1,4]benzodiazepine and 8-chloro-1-[(methylhyroxyamino)methyl]-6-phenyl-4H-s-triazolo[4,3-a][1,4]benzodiazepine which are separated from each other by chromatography as in Example 34.

EXAMPLE 42

8-Bromo-1-[[(dipropylamino)oxy]methyl]-6-(2-pyridyl)-4H-s-triazolo[4,3-a][1,4]benzodiazepine and 8-bromo-1-[(propylhydroxyamino)methyl]-6-(2-pyridyl)-4H-s-triazolo[4,3-a][1,4]benzodiazepine In the manner given in Example 34, 8-bromo-1-[(dipropylamino)methyl]-6-(2-pyridyl)-4H-s-triazolo[4,3-a]-[1,4]benzodiazepine $N^1$-oxide is heated between 140°–155° C. to give 8-bromo-1-[[(dipropylamino)oxy]-methyl]-6-(2-pyridyl)-4H-s-triazolo[4,3-a][1,4]benzodiazepine and 8-bromo-1-[(propylhydroxyamino)methyl]-6-(2-pyridyl)-4H-s-triazolo[4,3-a][1,4]benzodiazepine which are separated from each other by chromatography as in Example 34.

In the same manner given in Examples 34 to 42, other 6-phenyl- or respectively 6-(2-pyridyl)-1-[[(dialkylamino)oxy]methyl]-4H-s-triazolo[4,3-a][1,4]-benzodiazepines (IIIB) can be prepared and isolated. Representative compounds thus obtained include:

8-bromo-6-phenyl-1-[[(diethylamino)oxy]methyl]-4H-s-triazolo[4,3-a][1,4]benzodiazepine;

8-chloro-6-(o-fluorophenyl)-1-[[(ethylmethylamino)oxy]-methyl]-4H-s-triazolo[4,3-a][1,4]benzodiazepine;

8-chloro-6-(2,6-difluorophenyl)-1-[[(diethylamino)oxy]-methyl]-4H-s-triazolo[4,3-a][1,4]benzodiazepine;

6-(o-chlorophenyl)-1-[[(diethylamino)oxy]methyl]-4H-s-triazolo[4,3-a][1,4]benzodiazepine;

6-(o-fluorophenyl)-1-[[(ethylmethylamino)oxy]methyl]-4H-s-triazolo[4,3-a][1,4]benzodiazepine;

8-nitro-6-phenyl-1-[[(diethylamino)oxy]methyl]-4H-s-triazolo[4,3-a][1,4]benzodiazepine;

8-bromo-6-(o-chlorophenyl)-1-[[(ethylmethylamino)oxy]-methyl]-4H-s-triazolo[4,3-a][1,4]benzodiazepine;

8-trifluoromethyl-6-phenyl-1-[[(diethylamino)oxy]-methyl]-4H-s-triazolo[4,3-a][1,4]benzodiazepine;

8-fluoro-6-(o-chlorophenyl)-1-[ethylpropylamino oxy] methyl]-4H-s-triazolo[4,3-a][1,4]benzodiazepine;

8-fluoro-6-(o-fluorophenyl)-1-[[(ethylisopropylamino)-oxy]methyl]-4H-s-triazolo[4,3-a][1,4]benzodiazepine;

7-chloro-6-(o-chlorophenyl)-1-[[(diethylamino)oxy]-methyl]-4H-s-triazolo[4,3-a][1,4]benzodiazepine;

9-bromo-6-phenyl-1-[[(diethylamino)oxy]methyl]-4H-s-triazolo[4,3-a][1,4]benzodiazepine;

10-nitro-6-(o-fluorophenyl)-1-[[(diethylamino)oxy]-methyl]-4H-s-triazolo[4,3-a][1,4]benzodiazepine;

9-trifluoromethyl-6-(o-chlorophenyl)-1-[[(diethylamino)-oxy]methyl]-4H-s-triazolo[4,3-a][1,4]benzodiazepine;

8-chloro-6-(2-pyridyl)-1-[[(diethylamino)oxy]methyl]-4H-s-triazolo[4,3-a][1,4]benzodiazepine;

8-fluoro-6-(2-pyridyl)-1-[[(ethylmethylamino)oxy]-methyl]-4H-s-triazolo[4,3-a][1,4]benzodiazepine;

8-nitro-6-(2-pyridyl)-1-[[(diethylamino)oxy]methyl]-4H-s-triazolo[4,3-a][1,4benzodiazepine;

8-trifluoromethyl-6-(2-pyridyl)-1-[[(diethylamino)oxy]-methyl]-4H-s-triazolo[4,3-a][1,4]benzodiazepine;

7-nitro-6-(2-pyridyl)-1-[[(ethylmethylamino)oxy]methyl]-4H-s-triazolo[4,3-a][1,4]benzodiazepine;

9-bromo-6-(2-pyridyl)-1-[[(diethylamino)oxy]methyl]-4H-s-triazolo[4,3-a][1,4]benzodiazepine;

10-chloro-6-(2-pyridyl)-1-[[(diethylamino)oxy]methyl]-4H-s-triazolo[4,3-a][1,4]benzodiazepine;

8-bromo-6-phenyl-1-[[(dipropylamino)oxy]methyl]-4H-s-triazolo[4,3-a][1,4]benzodiazepine;

8-chloro-6-(o-fluorphenyl)-1-[[(ethylpropylamino)oxy]-methyl]-4H-s-triazolo[4,3-a][1,4]benzodiazepine;

8-chloro-6-(2,6-difluorophenyl)-1-[[(methylpropylamino-oxy]methyl]-4H-s-triazolo[4,3-a][1,4]benzodiazepine;

6-(o-chlorophenyl)-1-[[(dipropylamino)oxy]methyl]-4H-s-triazolo[4,3-a][1,4[benzodiazepine;

8-nitro-6-phenyl-1-[[(methylpropylamino)oxy]methyl]-4H-s-triazolo[4,3-a][1,4]benzodiazepine;

8-fluoro-6-(o-chlorophenyl)-1-[[(ethylpropylamino)oxy]-methyl]-4H-s-triazolo[4,3-a][1,4]benzodiazepine;

8-fluoro-6-(o-fluorophenyl)-1-[(methylpropylamino)-oxy]methyl]-4H-s-triazolo[4,3-a][1,4]benzodiazepine;

7-chloro-6-(o-chlorophenyl)-1-[[(dipropylamino)oxy]-methyl]-4H-s-triazolo[4,3-a][1,4]benzodiazepine;

10-nitro-6-(o-fluorophenyl)-1-[[(dipropylamino)oxy]-methyl]-4H-s-triazolo[4,3-a][1,4]benzodiazepine;

9-trifluoromethyl-6-(o-chlorophenyl)-1-[[(dipropylamino)oxy]methyl]-4H-s-triazolo[4,3-a][1,4]benzodiazepine;

8-chloro-6-(2-pyridyl)-1-[[(dipropylamino)oxy]methyl]-4H-s-triazolo[4,3-a][1,4]benzodiazepine;

8-fluoro-6-(2-pyridyl)-1-[[(methylpropylamino)oxy]-methyl]-4H-s-triazolo[4,3-a][1,4]benzodiazepine;

7-nitro-6-(2-pyridyl)-1-[[(ethylpropylamino)oxy]methyl]-4H-s-triazolo[4,3-a][1,4]benzodiazepine;

9-bromo-6-(2-pyridyl)-1-[[(dipropylamino)oxy]methyl]-4H-s-triazolo[4,3-a][1,4]benzodiazepine;

8-methylthio-6-phenyl-1-[[(diethylamino)oxy]methyl]-4H-s-triazolo[4,3-a][1,4]benzodiazepine;

8-methylthio-6-(2-pyridyl)-1-[[(ethylmethylamino)oxy]-methyl]-4H-s-triazolo[4,3-a][1,4]benzodiazepine;

8-ethylthio-6-(o-chlorophenyl)-1-[[(diethylamino)oxy]-methyl]-4H-s-triazolo[4,3-a][1,4]benzodiazepine;

8-propylthio-6-phenyl-1-[[(methylpropylamino)oxy]-methyl]-4H-s-triazolo[4,3-a][1,4]benzodiazepine;

1-[[(diethylamino)oxy]methyl]-6-phenyl-4H-s-triazolo[4,3-a][1,4]benzodiazepine;

8-methylthio-6-(2-pyridyl)-1-[[(diethylamino)oxy]-methyl]-4-H-s-triazolo[4,3-a][1,4benzodiazepine; and the like.

Also in the same manner given in Examples 32 to 40, other 6-phenyl- or respectively 6-(2-pyridyl)-1-[(alkylhydroxyamino)methyl]-4H-s-triazolo[4,3-a][1,4]benzodiazepines (V) can be prepared. Representative compounds thus obtained include:

8-bromo-6-phenyl-1-[(ethylhydroxyamino)methyl]-4H-s-triazolo[4,3-a][1,4-benzodiazepine;

8-chloro-6-(o-fluorophenyl)-1-[(ethylhydroxyamino)-methyl]-4H-s-triazolo[4,3-a][1,4]benzodiazepine;

8-chloro-6-(2,6-difluorophenyl)-1-[(ethylhydroxyamino)-methyl]-4H-s-triazolo[4,3-a][1,4]benzodiazepine;

6-(o-chlorophenyl)-1-[(ethylhydroxyamino)methyl]-4H-s-triazolo[4,3-a][1,4]benzodiazepine;

6-(o-fluorophenyl)-1-[(methylhdyroxyamino)methyl]-4H-s-triazolo[4,3-a][1,4]benzodiazepine;

8-nitro-6-phenyl-1-[(ethylhydroxyamino)methyl]-4H-s-triazolo[4,3-a][1,4]benzodiazepine;

8-bromo-6-(o-chlorophenyl)-1-[(methylhydroxyamino)methyl]-4H-s-triazolo[4,3-a][1,4]benzodiazepine;

8-trifluoromethyl-6-phenyl-1-[(ethylhydroxyamino)-methyl]-4H-s-triazolo[4,3-a][1,4]benzodiazepine;

8-fluoro-6-(o-chlorophenyl)-1-[(methylhydroxyamino)-methyl]-4H-s-triazolo[4,3-a][1,4]benzodiazepine;

8-fluoro-6-(o-fluorophenyl)-1-[(ethylhydroxyamino)-methyl]-4H-s-triazolo[4,3-a][1,4]benzodiazepine;

7-chloro-6-(o-chlorophenyl)-1-[(ethylhydroxyamino)-methyl]-4H-s-triazolo[4,3-a][1,4]benzodiazepine;

9-bromo-6-phenyl-1-[(ethylhydroxyamino)methyl]-4H-s-triazolo[4,3-a][1,4]benzodiazepine;

10-nitro-6-(o-fluorophenyl)-1-[(ethylhydroxyamino)-methyl]-4H-s-triazolo[4,3-a][1,4]benzodiazepine;

9-trifluoromethyl-6-(o-chlorophenyl)-1-[(methylhydroxyamino)methyl]-4H-s-triazolo[4,3-a][1,4]benzodiazepine;

8-chloro-6-(2-pyridyl)-1-[(methylhydroxyamino)methyl]-4H-s-triazolo[4,3-a][1,4-benzodiazepine;

8-fluoro-6-(2-pyridyl)-1-[(ethylhydroxyamino)methyl]-4H-s-triazolo[4,3-a][1,4]benzodiazepine;

8-nitro-6-(2-pyridyl)-1-[(ethylhydroxyamino)methyl]-4H-s-triazolo[4,3-a][1,4-]benzodiazepine;

8-trifluoromethyl-6-(2-pyridyl)-1-[(methylhydroxyamino)-methyl]-4H-s-triazolo[4,3-a][1,4]benzodiazepine;

7-nitro-6-(2-pyridyl)-1-[(ethylhydroxyamino)methyl]-4H-s-triazolo[4,3-a][1,4]benzodiazepine;

9-bromo-6-(2-pyridyl)-1-[(ethylhydroxyamino)methyl]-4H-s-triazolo[4,3-a][1,4]benzodiazepine;

10-chloro-6-(2-pyridyl)-1-[(methylhydroxymino)methyl]-4H-s-triazolo[4,3-a][1,4]benzodiazepine;

8-bromo-6-phenyl-1-[(propylhydroxyamino)methyl]-4H-s-triazolo[4,3-a][1,4]benzodiazepine;

8-chloro-6-(o-fluorophenyl)-1-[(propylhydroxyamino)-methyl]-4H-s-triazolo[4,3-a][1,4]benzodiazepine;

8-chloro-6-(2,6-difluorophenyl)-1-[(propylhydroxyamino)-methyl]-4H-s-triazolo[4,3-a][1,4]benzodiazepine;

6-(o-fluorophenyl)-1-[(propylhydroxyamino)methyl]-4H-s-triazolo[4,3-a][1,4]benzodiazepine;

8-nitro-6-phenyl-1-[(propylhydroxyamino)methyl]-4H-s-triazolo[4,3-a][1,4]benzodiazepine;

8-bromo-6-(o-chlorophenyl)-1-[(propylhydroxyamino)methyl]-4H-s-triazolo[4,3-a][1,4]benzodiazepine;

8-trifluoromethyl-6-phenyl-1-[(propylhydroxyamino)methyl]-4H-s-triazolo[4,3-a][1,4]benzodiazepine;

8-fluoro-6-(o-chlorophenyl)-1-[(isopropylhydroxyamino)-methyl]-4H-s-triazolo[4,3-a][1,4]benzodiazepine;

8-fluoro-6-(o-fluorophenyl)-1-[(isopropylhydroxyamino)-methyl]-4H-s-triazolo[4,3-a][1,4-benzodiazepine;

7-chloro-6-(o-chlorophenyl)-1-[(isopropylhydroxyamino)-methyl]-4H-s-triazolo[4,3-a][1,4]benzodiazepine;

9-trifluoromethyl-6-(o-chlorophenyl)-1-[(isopropylhydroxy-amino) ethyl]-4H-s-triazolo[4,3-a][1,4]benzodiazepine;

8-chloro-6-(2-pyridyl)-1-[(isopropylhydroxyamino)-methyl]-4H-s-triazolo[4,3-a][1,4]benzodiazepine;

[-methylthio-6-phenyl-1-[(ethylhdroxyamino)methyl]-4H-s-triazolo[4,3-a][1,4]benzodiazepine;

8-ethylthio-6-(o-chlorophenyl)-1-[(methylhydroxyamino)-methyl]-4H-s-triazolo[4,3-a][1,4]benzodiazepine;

8-propylthio-6-(2-pyridyl)-1-[(propylhydroxyamino)methyl]-4H-s-triazolo[4,3-a][1,4]benzodiazepine;

8-isopropylthio-6-(o-fluorophenyl)-1-[(ethylhydroxyamino)methyl]-4H-s-triazolo[4,3-a][1,4]benzodiazepine;

8-methylthio-6-(o-chlorophenyl)-1-[(methylhydroxyamino)-methyl]-4H-s-triazolo[4,3-a][1,4]benzodiazepine;

1-[(ethylhydroxyamino)methyl]-6-phenyl-4H-s-triazolo-[4,3-a][1,4]benzodiazepine;

8-methylthio-6-(2-pyridyl)-1-[(ethylhydroxyamino)-
methyl]-4H-s-triazolo[4,3-a][1,4]benzodiazepine;
and the like.

EXAMPLE 43

8-Chloro-1-[[(dimethylamino)oxy]methyl]-6-phenyl-
4H-s-triazolo[4,3-a][1,4]benzodiazepine A sample of 8-chloro-1-[(dimethylamino)methyl]-6-phenyl-4H-s-triazolo[4,3-a][1,4]benzodiazepine N$^1$-oxide hydrate (0.4 g.) was warmed under reduced pressure (34 mm) at 151°–161° C. for 8 minutes. During this time the solid melted with bubbling. The cooled melt was chromatographed on silica gel (50 g.) with 3% methanol 97% chloroform. The product thus obtained was crystalllized from ethyl acetate-Skellysolve B (hexanes) to give 8-chloro-1-[[(dimethylamino)oxy]methyl]-6-phenyl-4H-s-triazolo[4,3-a][1,4]benzodiazepine in two crops: 0.236 g. of melting point 175.5°–176.5° C. and 0.030 g. of melting point 174° C. The analytical sample had a melting point 175° C.

Anal. calcd. for $C_{19}H_{18}ClN_5O$: C, 62.04; H, 4.93; Cl, 9.64; N, 19.04. Found: C, 62.20; H, 5.06; Cl, 9.55; H, 19.17.

EXAMPLE 44

8-Chloro-1-[[(dimethylamino)oxy]methyl]-6-(o-chlorophenyl)-4H-s-triazolo[4,3-a][1,4]benzodiazepine In the manner given in Example 43, 8-chloro-1-[(dimethylamino)methyl]-6-(o-chlorophenyl)-4H-s-triazolo[4,3-a][1,4]benzodiazepine N$^1$-oxide was heated to 160° C. to give 8-chloro-[[(dimethylamino)oxy]methyl]-6-(o-chlorophenyl)-4H-s-triazolo[4,3-a][1,4]benzodiazepine.

EXAMPLE 45

8-Fluoro-1-[[(dimethylamino)oxy]methyl]-6-phenyl4H-s-triazolo[4,3-a][1,4]benzodiazepine In the manner given in Example 43, 8-fluoro-1-[(dimethylamino)methyl]-6-phenyl-4H-s-triazolo[4,3-a][1,4]-benzodiazepine N$^1$-oxide was heated to 160° C. to give 8-fluoro-1-[[(dimethylamino)oxy]methyl]-6-phenyl-4H-s-triazolo[4,3-a][1,4]benzodiazepine.

EXAMPLE 46

8-Trifluoromethyl-1-[[(dimethylamino)oxy]-methyl]-6-phenyl-4H-s-triazolo[4,3-a][1,4]benzodiazepine In the manner given in Example 43, 8-trifluoromethyl-1-[(dimethylamino)methyl]-6-phenyl-4H-s-triazolo[4,3-a]-[1,4]benzodiazepine N$^1$-oxide was heated to 160° C. to give 8-trifluoromethyl-1-[[(dimethylamino)oxy]methyl]-6-phenyl-4H-s-triazolo[4,3-a][1,4]benzodiazepine.

EXAMPLE 47

8-Nitro-1-[[(dimethylamino)oxy]methyl]-6-(o-chlorophenyl)-4H-s-triazolo[4,3-a][1,4]benzodiazepine In the manner given in Example 43, 8-nitro-1-[[(dimethylamino)methyl]-6-(o-chlorophenyl)-4H-s-triazolo-[4,3-a][1,4]benzodiazepine N$^1$-oxide was heated to 160° C. to give 8-nitro-1-[[(dimethylamino)oxy]methyl]-6-(o-chlorophenyl)-4H-s-triazolo[4,3-a][1,4]benzodiazepine.

EXAMPLE 48

8-Bromo-1-[[(dimethylamino)oxy]methyl]-6-(2-pyridyl)-4H-s-triazolo[4,3-a][1,4]benzodiazepine In the manner given in Example 43, 8-bromo-1-[(dimethylamino)methyl]-6-(2-pyridyl)-4H-s-triazolo[4,3-a]-[1,4]benzodiazepine N$^1$-oxide was heated to 160° C. to give 8-bromo-1-[[(dimethylamino)oxy]methyl]-6-(2-pyridyl)-4H-s-triazolo[4,3-a][1,4]benzodiazepine.

In the same manner given in Examples 43 to 48, combined with Example 15, other 6-phenyl- or respectively 6-(2-pyridyl)-1-[[(dimethylamino)oxy]methyl]-4H-s-triazolo[4,3-a][1,4]benzodiazepines (IIIB) can be prepared. Representative compounds thus obtained include:

8-methylthio-6-phenyl-1-[[(dimethylamino)oxy]methyl]4H-s-triazolo[4,3-a][1,4]benzodiazepine;
8-ethylthio-6-(o-chlorophenyl)-1-[[(dimethylamino)oxy]methyl]-4H-s-triazolo[4,3-a][1,4]benzodiazepine;
8-propylthio-6-(2-pyridyl)-1-[[(dimethylamino)oxy]methyl]-4H-s-triazolo[4,3-a][1,4]benzodiazepine;
8-isopropylthio-6-(o-fluorophenyl)-1-[[(dimethylamino)oxy]methyl]-4H-s-triazolo[4,3-a][1,4]benzodiaze pine;
8-methylthio-6-(2-pyridyl)-1-[[(dimethylamino)oxy]methyl]-4H-s-triazolo[4,3-a][1,4]benzodiazepine;
8-bromo-6-phenyl-1-[[(dimethylamino)oxy]methyl]-4H-s-triazolo[4,3-a][1,4]benzodiazepine;
8-chloro-6-(o-fluorophenyl)-1-[[(dimethylamino)oxy]methyl]-4H-s-triazolo[4,3-a][1,4]benzodiazepine;
8-chloro-6-(2,6-difluorophenyl)-1-[[(dimethylamino)oxy]methyl]-4H-s-triazolo[4,3-a][1,4]benzodiazepine;
8-trifluoromethyl-6-(o-chlorophenyl)-1-[[(dimethylamino)oxy]methyl]-4H-s-triazolo[4,3-a][1,4]benzodiazepine;
6-(o-fluorophenyl)-1-[[(dimethylamino)oxy]methyl]-4H-s-triazolo[4,3-a][1,4]benzodiazepine;
8-nitro-6-phenyl-1-[[(dimethylamino)oxy]methyl]-4H-s-triazolo[4,3-a][1,4]benzodiazepine;
8-bromo-6-(o-chlorophenyl)-1-[[(dimethylamino)oxy]methyl]-4H-s-triazolo[4,3-a][1,4]benzodiazepine;
8-trifluoromethyl-6-phenyl-1-[[(dimethylamino)oxy]methyl]-4H-s-triazolo[4,3-a][1,4]benzodiazepine;
8-fluoro-6-(o-chlorophenyl)-1-[[(dimethylamino)oxy]methyl]-4H-s-triazolo[4,3-a][1,4]benzodiazepine;
8-fluoro-6-(o-fluorophenyl)-1-[[(dimethylamino)oxy]methyl]-4H-s-triazolo[4,3-a][1,4]benzodiazepine;
7-chloro-6-(o-chlorophenyl)-1-[[(dimethylamino)oxy]-methyl]-4H-s-triazolo[4,3-a][1,4]benzodiazepine;
9-bromo-6-phenyl-1-[[(dimethylamino)oxy]methyl]-4H-s-triazolo[4,3-a][1,4]benzodiazepine;
10-nitro-6-(o-fluorophenyl)-1-[[(dimethylamino)oxy]methyl]-4H-s-triazolo[4,3-a][1,4]benzodiazepine;
9-trifluoromethyl-6-(o-chlorophenyl)-1-[[(dimethylamino)-oxyl]methyl]-4H-s-triazolo[4,3-a][1,4]benzodiazepine;
8-chloro-6-(2-pyridyl)-1-[[(dimethylamino)oxy]methyl]-4H-s-triazolo[4,3-a][1,4]benzodiazepine;
8-fluoro-6-(2-pyridyl)-1-[[(dimethylamino)oxy]methyl]-4H-s-triazolo[4,3-a][1,4]benzodiazepine;
8-nitro-6-(2-pyridyl)-1-[[(dimethylamino)oxy]methyl]-4H-s-triazolo[4,3-a][1,4]benzodiazepine;

8-trifluoromethyl-6-(2-pyridyl)-1-[[(dimethylamino)oxy]-methyl]-4H-s-triazolo[4,3-a][1,4]benzodiazepine;

7-nitro-6-(2-pyridyl)-1-[[(dimethylamino)oxy]methyl]-4H-s-triazolo[4,3-a][1,4]benzodiazepine;

9-bromo-6-(2-pyridyl)-1-[[(dimethylamino)oxy]methyl]-4H-s-triazolo[4,3-a][1,4]benzodiazepine;

10-chloro-6-(2-pyridyl)-1-[[(dimethylamino)oxy]methyl]-4H-s-traizolo[4,3-a][1,4]benzodiazepine; and the like.

EXAMPLE 49

O-[(8-Chloro-6-phenyl-4H-s-triazolo[4,3-a]-[1,4]benzodiazepin-1-yl)methyl]formaldehyde oxime A stirred mixture of 8-chloro-1-[(aminooxy)methyl]-6-phenyl-4H-s-triazolo[4,3-a][1,4]benzodiazepine (3.40 g., 0.01 mole), acetic acid (0.6 g., 0.01 mole), 37% aqueous formaldehyde (5 ml.) and absolute ethanol (30 ml.) was kept at ambient temperature for 1 hour, and concentrated in vacuo. The residue was mixed with water, neutralized with sodium bicarbonate and extracted with chloroform. The extract was washed with brine, dried over anhydrous sodium sulfate and concentrated. The residue was crystallized from ethyl acetate to give the O-[(8-chloro-6-phenyl-4H-s-triazolo[4,3-a][1,4]benzodiazepin1-yl)methyl]formaldehyde oxime of melting point 208.5°–210° C.

Anal. calcd. for $C_{18}H_{14}ClN_5O$: C, 61.46; H, 4.01; Cl, 10.08; N, 19.91. Found: C, 61.54; H, 4.04; Cl, 9.98; N, 19.97.

EXAMPLE 50

O-[(8-Chloro-6-phenyl-4H-s-triazolo[4,3-a]-[1,4]benzodiazepin-1-yl)methyl]acetone oxime A stirred mixture of 8-chloro-1[(aminooxy)methyl]-6-phenyl-4H-s-triazolo[4,3-a][1,4]benzodiazepine (3.40 g., 0.01 mole), acetic acid (0.6 g., 0.01 mole), acetone (3 ml.) and absolute ethanol (30 ml.) was refluxed under nitrogen for 1 hour and concentrated in vacuo. The residue was mixed with water, neutralized with sodium bicarbonate and extracted with chloroform. The extract was washed with brine, dried over anhydrous sodium sulfate and concentrated. The residue was crystallized from ethyl acetate-Skellysolve B hexanes to give O-[(8-chloro-6-phenyl-4H-s-triazolo[4,3-a][1,4]benzodiazepin-1-yl)-methyl]acetone oxime of melting point 168.5°–170° C.

Anal. calcd. for $C_{20}H_{18}ClN_5O$: C, 63.24; H, 4.78; Cl, 9.33; N, 18.44. Found: C, 62.74; H, 4.81; Cl, 9.44; N, 18.51.

EXAMPLE 51

O-[(8-Chloro-6-(o-chlorophenyl)-4H-s-triazolo-[4,3-a][1,4]benzodiazepin-1-yl)methyl]formaldehyde oxime In the manner given in Example 49, 8-chloro-1-[(aminooxy)methyl]-6-(o-chlorophenyl)-4H-s-triazolo-[4,3-a][1,4]benzodiazepine, acetic acid, formaline, and ethanol are reacted to give O-[(8-chloro-6-(o-chlorophenyl)-4H-s-triazolo[4,3-a][1,4]benzodiazepin-1-yl)-methyl]formaldehyde oxime.

EXAMPLE 52

O-[(8-Chloro-6-(o-chlorophenyl)-4H-s-triazolo-[4,3-a][1,4]benzodiazepin-1-yl)methyl]acetone oxime In the manner given in Example 50, 8-chloro-1-[(aminooxy)methyl]-6-(o-chlorophenyl)-4H-s-triazolo-[4,3-a][1,4]benzodiazepine, acetic acid, acetone and ethanol are reacted to give O-[(8-chloro-6-(o-chlorophenyl)-4H-s-triazolo[4,3-a][1,4]benzodiazepin-1-yl)-methyl]acetone oxime.

EXAMPLE 53

O-[(8-Fluoro-6-phenyl-4H-s-triazolo[4,3-a]-[1,4]benzodiazepin-1-yl)methyl]propionaldehyde oxime In the manner given in Example 49, 8-fluoro-1-[(aminooxy)methyl]-6-phenyl-4H-s-triazolo[4,3-a][1,4]-benzodiazepine, acetic acid, propionaldehyde, (instead of the formaldehyde of Example 49) and ethanol are reacted to give O-[(8-fluoro-6-phenyl-4H-s-triazolo[4,3-a][1,4]benzodiazepin-1-yl)methyl]propionaldehyde oxime.

EXAMPLE 54

O-[(8-Nitro-6-(o-chlorophenyl)-4H-s-triazolo[4,3-a][1,4]benzodiazepin-1-yl)methyl]methyl ethyl ketone oxime In the manner given in Example 50, 8-nitro-1-[(aminooxy)methyl]-6-phenyl-4H-s-triazolo[4,3-a][1,4]benzodiazepine, acetic acid, methyl ethyl ketone (instead of the acetone of Example 50) and ethanol are reacted to give O-[(8-nitro-6-(o-chlorophenyl)-4H-s-triazolo[4,3-a][1,4]benzodiazepin-1-yl)methyl]methyl ethyl ketone oxime.

EXAMPLE 55

O-[(8-Trifluoromethyl-6-(o-chlorophenyl)-4H-s-triazolo[4,3-a][1,4]benzodiazepin-1-yl)methyl]-formaldehyde oxime In the manner given in Example 49, 8-trifluoromethyl-1-[(aminooxy)methyl]-6-(o-chlorophenyl)-4H-s-triazolo[4,3-a][1,4]benzodiazepine, acetic acid, formaline and ethanol are reacted to give O-[(8-trifluoromethyl-6-(o-chlorophenyl)-4H-s-triazolo[4,3-a][1,4]benzodiazepin1-yl)methyl]formaldehyde oxime.

EXAMPLE 56

O-[(8-Bromo-6-(2-pyridyl)-4H-s-triazolo[4,3-a][1,4]benzodiazepin-1-yl)methyl]formaldehyde oxime In the manner given in Example 49, 8-bromo-1-[(aminooxy)methyl]-6-(2-pyridyl)-4H-s-triazolo[4,3-a][1,4]benzodiazepine, acetic acid, formaline and ethanol are reacted to give O-[(8-bromo-6-(2-pyridyl)-4H-s-triazolo[4,3-a][1,4]benzodiazepin-1-yl)methyl]formaldehyde oxime.

EXAMPLE 57

O-[(8-Bromo-6-(2-pyridyl)-4H-s-triazolo[4,3-a][1,4]benzodiazepin-1-yl)methyl]acetone oxime In the manner given in Example 50, 8-bromo-1-[(aminooxy)methyl]-6-(2-pyridyl)-4H-s-triazolo[4,3-a][1,4]benzodiazepine, acetic acid, acetone and ethanol are reacted to give O-[(8-bromo-6-(2-pyridyl)-4H-s-triazolo[4,3-a][1,4]benzodiazepin-1-yl)methyl]acetone oxime.

EXAMPLE 58

O-[(8-Bromo-6-(2-pyridyl)-4H-s-triazolo[4,3-a][1,4]benzodiazepin-1-yl)methyl]methyl ethyl ketone oxime In the manner given in Example 50, 8-bromo-1-[(aminooxy)methyl]-6-(2-pyridyl)-4H-s-triazolo[4,3-a]-[1,4]benzodiazepine, acetic acid, methyl ethyl ketone and ethanol are reacted to give O-[(8-bromo-6-(2- pyridyl)-4H-s-triazolo[4,3-a][1,4]benzodiazepin-1-yl)methyl]-methyl ethyl ketone oxime.

In the manner given in the preceding Examples 47 to 58, other Schiffs bases of compounds of formula IIIA can be made. Representative compounds, thus obtained, include:

O-[(8-bromo-6-phenyl-4H-s-triazolo[4,3-a][1,4]-benzodiazepin-1-yl)methyl]formaldehyde oxime;

O-[(8-chloro-6-(o-fluorophenyl)-4H-s-triazolo[4,3-a]-[1,4]-benzodiazepin-1-yl)methyl]formaldehyde oxime;

O-[(8-chloro-6-(2,6-difluorophenyl)-4H-s-triazolo[4,3-a]-[1,4]benzodiazepin-1-yl)methyl]formaldehyde oxime;

O-[(6-(o-chlorophenyl)-4H-s-triazolo[4,3-a][1,4]benzodiazepin-1-yl)methyl]formaldehyde oxime;

O-[(6-(o-fluorophenyl)-4H-s-triazolo]4,3-a][1,4]benzodiazepin-1-yl)methyl]formaldehyde oxime;

O-[(8-nitro-6-phenyl-4H-s-triazolo[4,3-a][1,4]benzodiazepin-1-yl)methyl]formaldehyde oxime;

O-[(8-bromo-6-(o-chlorophenyl)-4H-s-triazolo[4,3-a][1,4]-benzodiazepin-1-yl)methyl]formaldehyde oxime;

O-[(8-trifluoromethyl-6-phenyl-4H-s-triazolo[4,3-a][1,4]-benzodiazepin-1-yl)methyl]formaldehyde oxime;

O-[(8-fluoro-6-(o-chlorophenyl)-4H-s-triazolo[4,3-a][1,4]-benzodiazepin-1-yl)methyl]formaldehyde oxime;

O-[(8-fluoro-6-(o-fluorophenyl)-4H-s-triazolo[4,3-a]-[1,4]benzodiazepin-1-yl)methyl]formaldehyde oxime;

O-[(7-chloro-6-(o-chlorophenyl)-4H-s-triazolo[4,3-a]-[1,4]benzodiazepin-1-yl)methyl]formaldehyde oxime;

O-[(9-bromo-6-phenyl-4H-s-triazolo[4,3-a][1,4]benzodiazepin-1-yl)methyl]formaldehyde oxime;

O-[(10-nitro-6-(o-fluorophenyl)-4H-s-triazolo[4,3-a]-[1,4]benzodiazepin-1-yl)methyl]formaldehyde oxime;

O-[(9-trifluoromethyl-6-(o-chlorophenyl)-4H-s-triazolo-[4,3-a][1,4]benzodiazepin-1-yl)methyl]formaldehyde oxime;

O-[(8-chloro-6-(2-pyridyl)-4H-s-triazolo[4,3-a][1,4]-benzodiazepin-1-yl)methyl]formaldehyde oxime;

O-[(8-fluoro-6-(2-pyridyl)-4H-s-triazolo[4,3-a][1,4]-benzodiazepin-1-yl)methyl]formaldehyde oxime;

O-[(8-nitro-6-(2-pyridyl)-4H-s-triazolo[4,3-a][1,4]-benzodiazepin-1-yl)methyl]formaldehyde oxime;

O-[(8-trifluoromethyl-6-(2-pyridyl)-4H-s-triazolo[4,3-a]-[1,4]benzodiazepin-1-yl)methyl]formaldehyde oxime;

O-[(7-nitro-6-(2-pyridyl)-4H-s-triazolo[4,3-a][1,4]-benzodiazepin-1-yl)methyl]formaldehyde oxime;

O-[(9-bromo-6-(2-pyridyl)-4H-s-triazolo[4,3-a][1,4]-benzodiazepin-1-yl)methyl]formaldehyde oxime;

O-[(10-chloro-6-(2-pyridyl)-4H-s-triazolo[4,3-a][1,4]-benzodiazepin-1-yl)methyl]formaldehyde oxime;

O-[(8-bromo-6-phenyl-4H-s-triazolo[4,3-a][1,4]benzodiazepin-1-yl)methyl]acetone oxime;

O-[(8-chloro-6-(o-fluorophenyl)-4H-s-triazolo[4,3-a]-[1,4]benzodiazepin-1-yl)methyl]acetone oxime;

O-[(8-chloro-6-(2,6-difluorophenyl)-4H-s-triazolo[4,3-a]-[1,4]benzodiazepin-1-yl)methyl]acetone oxime;

O-[(6-(o-chlorophenyl)-4H-s-triazolo[4,3-a][1,4]benzodiazepin-1-yl)methyl]acetone oxime;

O-[(6-(o-fluorophenyl)-4H-s-triazolo[4,3-a][1,4]benzodiazepin-1-yl)methyl]acetone oxime;

O-[(8-nitro-6-phenyl-4H-s-triazolo[4,3-a][1,4]benzodiazepin-1-yl)methyl]acetone oxime;

O-[(8-bromo-6-(o-chlorophenyl)-4H-s-triazolo[4,3-a]-[1,4]benzodiazepin-1-yl)methyl]acetone oxime;

O-[(8-trifluoromethyl-6-phenyl-4H-s-triazolo[4,3-a]-[1,4]benzodiazepin-1-yl)methyl]acetone oxime;

O-[(8-fluoro-6-(o-chlorophenyl)-4H-s-triazolo[4,3-a]-[1,4]benzodiazepin-1-yl)methyl]acetone oxime;

O-[(8-fluoro-6(o-fluorophenyl)-4H-s-triazolo[4,3-a][1,4]-benzodiazepin-1-yl)methyl]acetone oxime;

O-[(7-chloro-6-(o-chlorophenyl)-4H-s-triazolo[4,3-a]-[1,4]benzodiazepin-1-yl)methyl]acetone oxime;

O-[(9-bromo-6-phenyl-4H-s-triazolo[4,3-a][1,4]benzodiazepin-1-yl)methyl]acetone oxime;

O-[(10-nitro-6-(o-fluorophenyl)-4H-s-triazolo[4,3-a]-[1,4]benzodiazepin-1-yl)methyl]acetone oxime;

O-[(9-trifluoromethyl-6-(o-chlorophenyl)-4H-s-triazolo[4,3-a][1,4]benzodiazepin-1-yl)methyl]acetone oxime;

O-[(8-chloro-6-(2-pyridyl)-4H-s-triazolo[4,3-a][1,4]-benzodiazepin-1-yl)methyl]acetone oxime;

O-[(8-fluoro-6-(2-pyridyl)-4H-s-triazolo[4,3-a][1,4]-benzodiazepin-1-yl)methyl]acetone oxime;

O-[(8-nitro-6-(2-pyridyl)-4H-s-triazolo[4,3-a][1,4]-benzodiazepin-1-yl)methyl]acetone oxime;

O-[(8-trifluoromethyl-6-(2-pyridyl)-4H-s-triazolo[4,3-a]-[1,4]benzodiazepin-1-yl)methyl]acetone oxime;

O-[(7-nitro-6-(2-pyridyl)-4H-s-triazolo[4,3-a][1,4]-benzodiazepin-1-yl)methyl]acetone oxime;

O-[(9-bromo-6-(2-pyridyl)-4H-s-triazolo[4,3-a][1,4]-benzodiazepin-1-yl)methyl]acetone oxime;

O-[(10-chloro-6-(2-pyridyl)-4H-s-triazolo[4,3-a][1,4]-benzodiazepin-1-yl)methyl]acetone oxime;

O-[(8-methylthio-6-phenyl-4H-s-triazolo[4,3-a][1,4]-benzodiazepin-1-yl)methyl]acetone oxime;

O-[(8-ethylthio-6-(o-chlorophenyl)-4H-s-triazolo[4,3-a]-[1,4]benzodiazepin-1-yl)methyl]formaldehyde oxime;

O-[(8-propylthio-6-(2-pyridyl)-4H-s-triazolo[4,3-a]-[1,4]benzodiazepin-1-yl)methyl]acetone oxime;

O-[(8-isopropylthio-6-(o-fluorophenyl)-4H-s-triazolo-[4,3-a][1,4]benzodiazepin-1-yl)methyl]acetone oxime;

O-[(6-phenyl-4H-s-triazolo[4,3-a][1,4]benzodiazepin-1-yl)-methyl]formaldehyde oxime; and the like.

EXAMPLE 59

8-Chloro-1-[[(methylamino)oxy]methyl]-6-phenyl-4H-s-triazolo[4,3-a][1,4]benzodiazepine A stirred solution of 8-chloro-1-[(aminooxy)methyl]-6-phenyl-4H-s-triazolo[4,3-a][1,4]benzodiazepine (0.02 mole) in dry dimethylformamide (50 ml.) is cooled in an ice bath under nitrogen and treated successively with a 57% mineral oil suspension of sodium hydride (0.84 g., 0.02 mole) and methyliodide (0.02 mole). The mixture is allowed to come slowly to ambient temperature and stand for 18 hours. It is then concentrated in vacuo. The residue is chromatographed on silica gel with methanol to give 8-chloro-1-[[(methylamino)oxy]methyl]-6-phenyl-4H-s-triazolo[4,3-a][1,4]benzodiazepine.

Using the procedure of Example 59 but substituting other 1-[(aminooxy)methyl]-6-phenyl- or 6-(2-pyridyl)-4H-s-triazolo[4,3-a][1,4]benzodiazepines for 8-chloro-1-[(aminooxy)methyl]-6-phenyl-4H-s-triazolo[4,3-a]-[1,4]benzodiazepine and other alkyl halides for methyl iodide other 1-[[(monoalkylamino)oxy]methyl]-6-phenyl or 6-(2-pyridyl)-4H-s-triazolo[4,3-a][1,4-benzodiazepines of formula III can be prepared.

The pharmacologically acceptable acid addition salts of compounds of formulae III, IV, V, VA, and VI can be prepared and isolated by conventional processes, such as reacting a compound of said formula with a selected pharmacologically acceptable acid. Such acids include hydrochloric, hydrobromic, phosphoric, sulfuric, acetic, tartaric, lactic, citric, malic, maleic, methanesulfonic, benzenesulfonic, cyclohexanesulfamic acids, toluenesulfonic, and the like. The reaction is conveniently performed in an organic solvent, e.g. ether, dioxane, or tetrahydrofuran, ethanol, methanol, or ethyl acetate; the salts can be recovered by crystallization, precipitation or evaporation of the solvent. These salts are useful in the same manner as the free base.

I claim:

1. A compound of the formula VI:

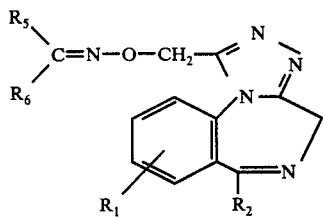

VI wherein $R_5$ and $R_6$ are hydrogen, or alkyl of 1 to 3 carbon atoms, inclusive; $R_1$ is hydrogen, fluoro, chloro, bromo, nitro, trifluoromethyl, or alkylthio in which the alkyl moiety is of 1 to 3 carbon atoms, inclusive; $R_2$ is phenyl, o-chlorophenyl, o-fluorophenyl, 2,6-difluorophenyl, and 2-pyridyl; and the pharmacologically acceptable acid addition salts thereof.

2. The compound according to claim 1, wherein $R_5$ and $R_6$ are hydrogen; $R_1$ is 8-bromo; $R_2$ is 2-pyridyl and the compound is therefore O-[(8-bromo-6-(2-pyridyl)-4H-s-triazolo[4,3-a]1,4]benzodiazepin-1-yl)methyl]formaldehyde oxime.

3. The compound according to claim 1, wherein $R_5$ and $R_6$ are methyl; $R_1$ is 8-bromo; $R_2$ is 2-pyridyl; and the compound is therefore O-[(8-bromo-6-(2-pyridyl)-4H-s-triazolo[4,3-a][1,4]benzodiazepin-1-yl)methyl]acetone oxime.

4. The compound according to claim 1, wherein $R_5$ and $R_6$ are hydrogen; $R_1$ is 8-chloro; $R_2$ is phenyl and the compound is therefore O-[(8-chloro-6-phenyl-4H-s-triazolo-[4,3-a][1,4]benzodiazepin-1-yl)methyl]formaldehyde oxime.

5. The compound according to claim 1, wherein $R_5$ and $R_6$ are hydrogen, $R_1$ is 8-chloro, $R_2$ is o-chlorophenyl, and the compound is therefore O-[(8-chloro-6-(o-chlorophenyl)-4H-s-triazolo[4,3-a][1,4]benzodiazepin-1-yl)methyl]-formaldehyde oxime.

6. The compound according to claim 1, wherein $R_5$ is hydrogen; $R_6$ is ethyl, $R_1$ is 8-fluoro, $R_2$ is phenyl and the compound is therefore O-[(8-fluoro-6-phenyl-4H-s-triazolo[4,3-a][1,4]benzodiazepin-1-yl)methyl]-propionaldehyde oxime.

7. The compound according to claim 1, wherein $R_5$ and $R_6$ are methyl, $R_1$ is 8-chloro, $R_2$ is phenyl and the compound is therefore O-[(8-chloro-6-phenyl-4H-s-triazolo[4,3-a][1,4]benzodiazepin-1-yl)methyl]acetone oxime.

8. The compound of claim 1, wherein $R_5$ and $R_6$ are methyl, $R_1$ is 8-chloro, $R_2$ is o-chlorophenyl and the compound is therefore O-[(8-chloro-6-(o-chlorophenyl)-4H-s-triazolo[4,3-a][1,4]benzodiazepin-1-yl)methyl]-acetone oxime.

* * * * *

UNITED STATES PATENT AND TRADEMARK OFFICE
CERTIFICATE OF CORRECTION

PATENT NO. : 4,081,452
DATED : March 28, 1978
INVENTOR(S) : Jackson B. Hester, Jr.

It is certified that error appears in the above-identified patent and that said Letters Patent are hereby corrected as shown below:

Column 34, line 6: "[4,3-a]1,4]" should read -- [4,3-a][1,4] --

Signed and Sealed this

Twenty-sixth Day of June 1979

[SEAL]

Attest:

RUTH C. MASON
Attesting Officer

DONALD W. BANNER
Commissioner of Patents and Trademarks